United States Patent [19]
Wolin et al.

[11] Patent Number: 5,595,998
[45] Date of Patent: Jan. 21, 1997

[54] PYRAZOLOQUINOLINES

[76] Inventors: Ronald L. Wolin, 406 Mountain Ave., Westfield, N.J. 07090; Adriano Afonso, 10 Woodmere Rd., West Caldwell, N.J. 07006; Joseph M. Kelly, 112 Princeton Rd., Parlin, N.J. 08859; F. George Njoroge, 2597 Juliat Pl., Union, N.J. 07083

[21] Appl. No.: 357,624

[22] Filed: Dec. 15, 1994

[51] Int. Cl.$^6$ .................. C07D 471/14; C07D 487/14; A61K 31/44
[52] U.S. Cl. .................................... 514/293; 546/82
[58] Field of Search .................... 546/82; 514/293

[56] References Cited

PUBLICATIONS

Nucleic Acids Research, vol. 17, No. 15 (1989) pp. 6129–6141.
Chem. Lett. (1978)(6) pp. 605–608 (a computer printout of an abstract is enclosed).
J. Org. Chem. (1968) 33(5), 1806–10 (a computer printout of an abstract is enclosed).

*Primary Examiner*—Alan L. Rotman
*Attorney, Agent, or Firm*—Matthew Boxer; John Maitner

[57] ABSTRACT

The invention relates to compounds of the formulas

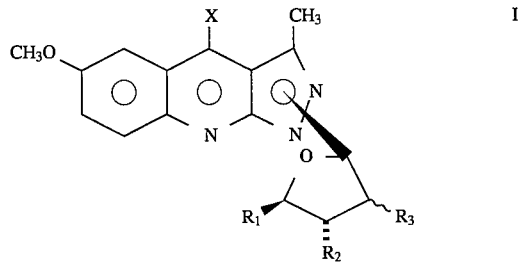

wherein X, $R_1$, $R_2$, and $R_3$, are as described herein.

These compounds are useful as antitumor agents. Pharmaceutical compositions containing compounds of formula I are also described. Methods for treating tumors which comprise administration of compounds of formula I are also described. Processes for preparing compounds of formula I are also described.

17 Claims, No Drawings

PYRAZOLOQUINOLINES

SUMMARY OF THE INVENTION

The invention relates to compounds of the formulas

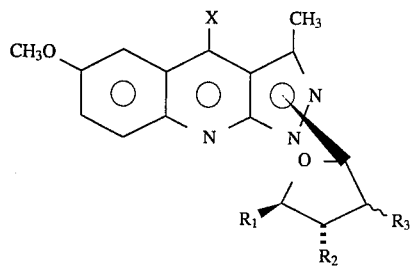

I wherein $R_1$ is HO—$CH_2$; ($C_1$–$C_6$)-alkyl-O—$CH_2$; $NH_2CH_2$; $PhCH_2COOCH_2$; $PhCH_2OCH_2$; $PhCOCH_2CH(OH)$; $PhCOCH_2CH_2$; $PhCONHCH_2$; ($C_1$–$C_6$)-alkyl-$COOCH_2$; 3-Py$COOCH_2$; 2-Fu—$COOCH_2$; 3-Fu$COOCH_2$; PhCOCH=CH; $PhCOOCH_2$; or substituted-$PhCOOCH_2$, wherein the substituents are selected from the group consisting of ($C_1$–$C_6$)alkyl, ($C_1$–$C_6$)alkoxy, and nitro;

$R_2$ and $R_3$ are each independently HO; ($C_1$–$C_6$)-alkyl-COO; $PhCH_2COO$; 3-FuCOO; 2-FuCOO; $PhCH_2O$; 3-PyCOO; PhCOO; substituted-PhCOO wherein the substituents are selected from the group consisting of ($C_1$–$C_6$)alkyl, ($C_1$–$C_6$)alkoxy, and nitro; or $R_2$ and $R_3$ taken together can be a chemical bond;

and with the proviso that when the bond attached to the $R_2$ and the bond attached to the $R_3$ both extend below the plane of the page that $R_2$ and $R_3$ taken together can be

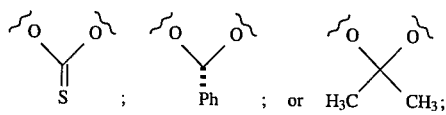

and

X is Cl or H;

or a stereoisomer thereof, or a pharmaceutically acceptable salt thereof.

As used herein 3-Fu means

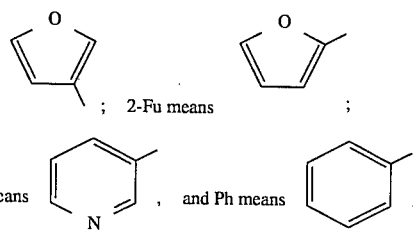
; 2-Fu means ;

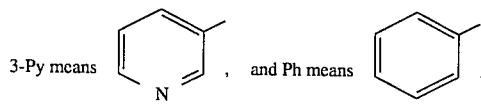

3-Py means , and Ph means .

Preferred are compounds of the formula

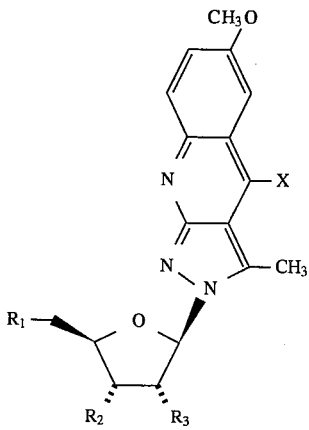

I'' wherein $R_1$ is HO—$CH_2$; ($C_1$–$C_6$)-alkyl-O—$CH_2$; $NH_2CH_2$; $PhCH_2COOCH_2$; $PhCH_2OCH_2$; $PhCOCH_2C(OH,H)$; $PhCOCH_2CH_2$; $PhCONHCH_2$; ($C_1$–$C_6$)-alkyl-$COOCH_2$; 3-Py$COOCH_2$; 2-Fu—$COOCH_2$; 3-Fu$COOCH_2$; PhCOCH=CH; $PhCOOCH_2$; or substituted-$PhCOOCH_2$, wherein the substituents are selected from the group consisting of ($C_1$–$C_6$)alkyl, ($C_1$–$C_6$)alkoxy, and nitro;

$R_2$ and $R_3$ are each independently HO; ($C_1$–$C_6$)-alkyl-COO; $PhCH_2COO$; 3-FuCOO; 2-FuCOO; $PhCH_2O$; 3-PyCOO; PhCOO; substituted-PhCOO wherein the substituents are selected from the group consisting of ($C_1$–$C_6$)alkyl, ($C_1$–$C_6$)alkoxy, and nitro; or $R_2$ and $R_3$ taken together can be a chemical bond;

and with the proviso that when the bond attached to the $R_2$ and the bond attached to the $R_3$ both extend below the plane of the page that $R_2$ and $R_3$ taken together can be

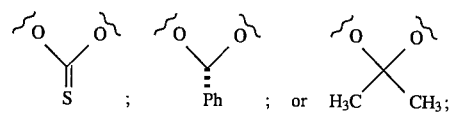

and

X is Cl or H.

Also preferred are compounds of the formula

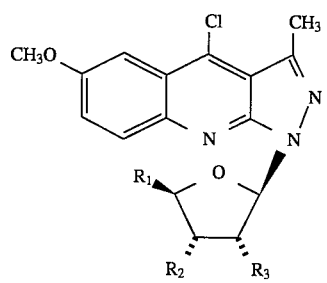

I' wherein $R_1$ is HO—$CH_2$; ($C_1$–$C_6$)-alkyl-O—$CH_2$; $NH_2CH_2$; $PhCH_2COOCH_2$; $PhCH_2OCH_2$; $PhCOCH_2C(OH,H)$; $PhCOCH_2CH_2$; $PhCONHCH_2$; $PyCOOCH_2$; 2-Fu—$COOCH_2$; 3-Fu$COOCH_2$; PhCOCH=CH; $PhCOOCH_2$; or substituted-Ph-$COOCH_2$, wherein the substituents are selected from the group consisting of ($C_1$–$C_6$)alkyl, ($C_1$–$C_6$)alkoxy, and nitro;

$R_2$ and $R_3$ are each independently HO; ($C_1$–$C_6$)-alkyl-COO; $PhCH_2COO$; 3-FuCOO; 2-FuCOO; $PhCH_2O$—;

3-PyCOO; PhCOO—; substituted-PhCOO— wherein the substituents are selected from the group consisting of ($C_1$–$C_6$)alkyl, ($C_1$–$C_6$)alkoxy, and nitro; or $R_2$ and $R_3$ taken together can be a chemical bond;

and with the proviso that when the bond attached to the $R_2$ and the bond attached to the $R_3$ both extend below the plane of the page that $R_2$ and $R_3$ taken together can be

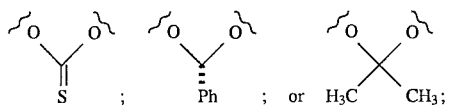

and

X is Cl, H, or OH.

Also preferred compounds of formula I' wherein $R_1$ is PhCOOCH$_2$; or substituted-PhCOOCH$_2$, wherein the substituents are selected from the group consisting of ($C_1$–$C_6$)alkyl, ($C_1$–$C_6$)alkoxy, and nitro;

Also preferred compounds of formula I' wherein $R_1$ is PhCOOCH$_2$.

Also preferred compounds of formula I' wherein $R_2$ and $R_3$ are each independently PhCOOCH$_2$; or substituted-PhCOOCH$_2$, wherein the substituents are selected from the group consisting of ($C_1$–$C_6$)alkyl, ($C_1$–$C_6$)alkoxy, and nitro.

Also preferred compounds of the formula

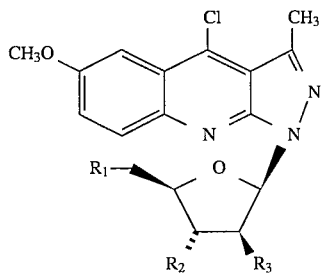

wherein $R_1$ is HO—CH$_2$; ($C_1$–$C_6$)-alkyl-O—CH$_2$; NH$_2$CH$_2$; PhCH$_2$COOCH$_2$; PhCH$_2$OCH$_2$; PhCOCH$_2$CH(OH); PhCOCH$_2$CH$_2$; PhCONHCH$_2$; ($C_1$–$C_6$)-alkyl—COOCH$_2$; 3-PyCOOCH$_2$; 2-Fu—COOCH$_2$; 3-FuCOOCH$_2$; PhCOCH=CH; PhCOOCH$_2$; or substituted-PhCOOCH$_2$, wherein the substituents are selected from the group consisting of ($C_1$–$C_6$)alkyl, ($C_1$–$C_6$)alkoxy, and nitro;

$R_2$ and $R_3$ are each independently HO; ($C_1$–$C_6$)-alkyl-COO; PhCH$_2$COO; 3-FuCOO; 2-FuCOO; PhCH$_2$O—; 3-PyCOO; PhCOO—; substituted-PhCOO— wherein the substituents are selected from the group consisting of ($C_1$–$C_6$)alkyl, ($C_1$–$C_6$)alkoxy, and nitro; or $R_2$ and $R_3$ taken together can be a chemical bond.

Exemplary of compounds of the invention are:

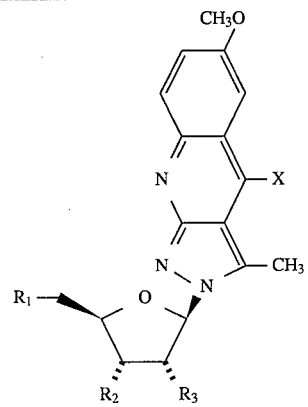

| X | $R_1$ | $R_2$ | $R_3$ | Ras p21 Assay |
|---|---|---|---|---|
| Cl | O(CO)Ph | O(CO)Ph | O(CO)Ph | 10 μM |
| H | O(CO)Ph | O(CO)Ph | O(CO)Ph | 8 μM |
| Cl | OH | OH | OH | 0% (100) |
| OH | OH | OH | OH | 49% (100) |
| OH | O(CO)Ph | O(CO)Ph | O(CO)Ph | 10 μM |
| Cl | O(CO)Ph | OH | OH | 49% (100) |
| Cl | O(CO)Ph | OCOCH$_3$ | OCOCH$_3$ | 20% (100) |
| Cl | O(CO)Ph | —OC(S)O— | | 86% (100) |

The biological data shown in the table above and throughout this specification is from the ras p21 Nucleotide Exchange Assay which is described below.

Another compound of the invention is derived from an arabinose and has the structure:

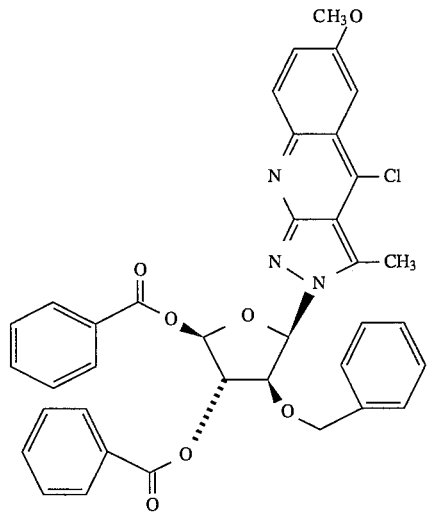

which showed 32% (50 μM) in the ras p21 assay.

Other exemplary compounds of the invention are:

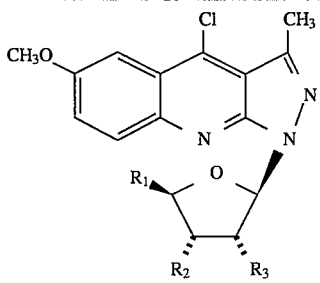

I'

| R₁ | R₂ | R₃ | ras p21 Assay |
|---|---|---|---|
| O(CO)Ph | O(CO)Ph | O(CO)Ph | 10 μM |
| OCOCH₃ | O(CO)CH₃ | O(CO)CH₃ | 3% (100 μM) |
| CH₂Ph | CH₂Ph | CH₂Ph | 35% (100 μM) |
| O(CO)CH₂Ph | (CO)CH₂Ph | O(CO)CH₂Ph | 62% (100 μM) |
| O(CO)Ph-2,5-(CH₃)₂ | (CO)Ph-2,5-(CH₃)₂ | O(CO)Ph-2,5-(CH₃)₂ | 37% (100 μM) |
| O(CO)Ph-4-CH₃O | (CO)Ph-4-CH₃O | O(CO)Ph-4-CH₃O | 44% (100 μM) |
| O(CO)Ph-4-NO₂ | (CO)Ph-4-NO₂ | O(CO)Ph-4-NO₂ | 59% (100 μM) |
| O(CO)Ph | OH | OH | 16% (100 μM) |
| OH | OH | OH |  |
| OH |  | —OC(CH₃)₂—O— | 11% (100 μM) |
| O(CO)-2-Fu | O(CO)-2-Fu | O(CO)-2-Fu | 10 μM |
| O(CO)Py | O(CO)Py | O(CO)Py | 33% (50 μM) |
| O(CO)-3-Fu | O(CO)-3-Fu | O(CO)-3-Fu | 49% (50 μM) |
| O(CO)—CH₂CH(CH₃)₂ | O(CO)—CH₂CH(CH₃)₂ | O(CO)—CH₂CH(CH₃)₂ | 33% (50 μM) |
| C(H,OH)CH₂(CO)Ph |  | —OC(S)O— | 1.5 μM |
| (CO)Ph | —OC(S)O— |  | 15 μM |
| O(CO)Ph | —OC(Ph)O— |  | 41% (100 μM) |
| O(CO)Ph | O(CO)—CH₃ | O(CO)—CH₃ | 44% (100 μM) |
| O(CO)Ph | —CH₂Ph | —CH₂Ph | 53% (100 μM) |
| O(CO)Ph | — |  | 90 μM |
| NH₂ |  | —OC(CH₃)₂—O— | 38% (50 μM) |
| O(CO)PhNH |  | —OC(CH₃)₂—O— | 56% (50 μM) |
| O(CO)PhNH | OH | OH | 24% (50 μM) |

* The straight line under R₂ and R₃ is intended to denote the following double bond shown in the structure below by an arrow:

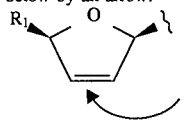

Another compound of the invention is

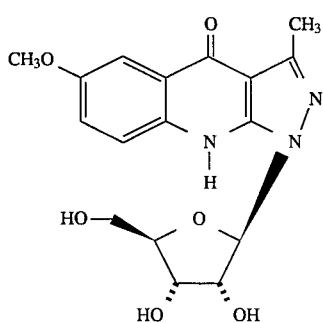

(This compound may be prepared by reacting

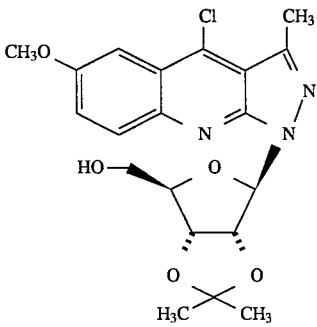

with a hydrolyzing agent such as 3NCHl).

Other compounds of the invention are

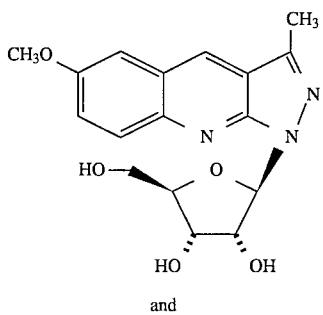

and

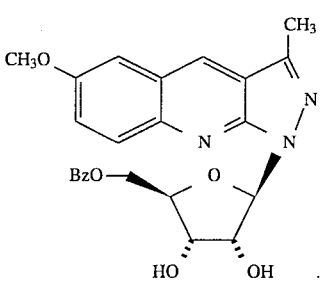

The second of these two compounds mentioned just above has an IC$_{50}$ in the ras p 21 assay of 50 μM.

Treating

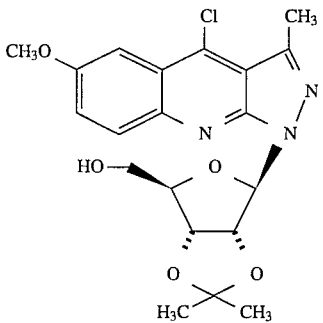

with N,N-dimethylethanolamine and NaH and then by treating the resulting product with benzoyl chloride results in the acetonide

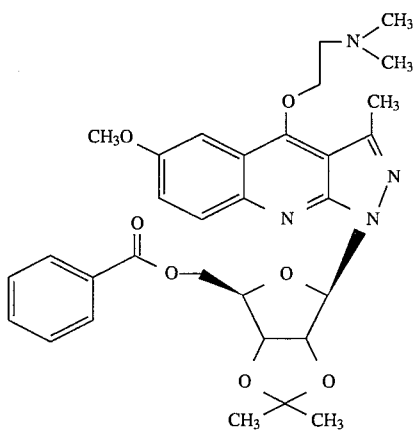

which is a compound of the invention. This latter compound showed 59% inhibition at 100 μM in the ras p 21 assay.

This acetonide is hydrolyzed and then treated with benzoyl chloride

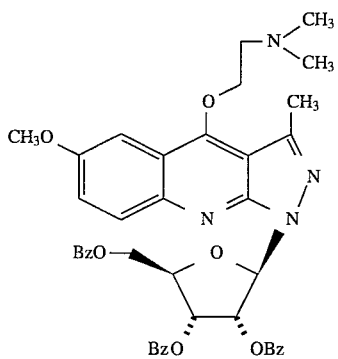

so as to result in the compound
which is also a compound of the invention. This latter compound showed 12% inhibition at 100 μM in the ras p 21 assay.

Another compound of the invention is

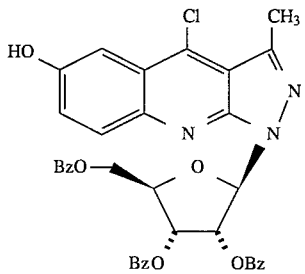

which has an IC$_{50}$=10 μM in the ras p21 Nucleotide Exchange Assay.

This compound is prepared by procedures analogous to those set forth herein. Preparation of the hydroxy-containing pyrazoloquinoline starting material used in making this compound can be accomplished by methods analogous to those set forth in copending Ser. No. 08/164,238 filed Dec. 9, 1993, which is hereby incorporated by reference.

Another compound of the invention is

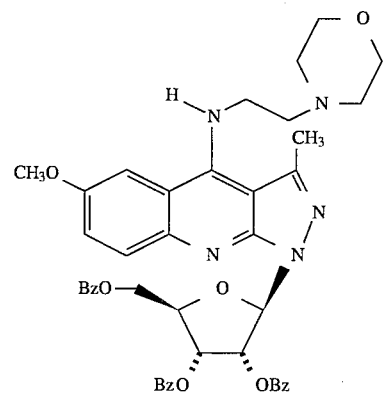

which has an 86% inhibition at 100 μM in the ras p21 Nucleotide Exchange Assay.

Still other compounds of the invention are:

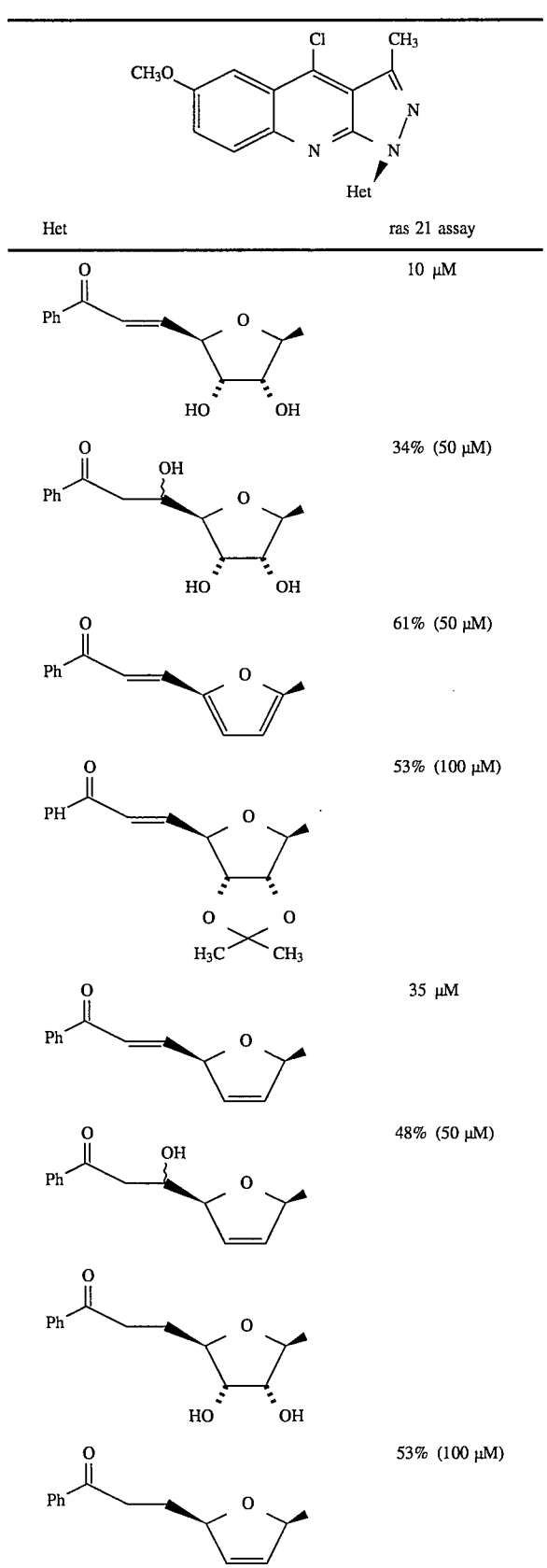

Other exemplary of compounds of the invention are the following which are derived from arabinose:

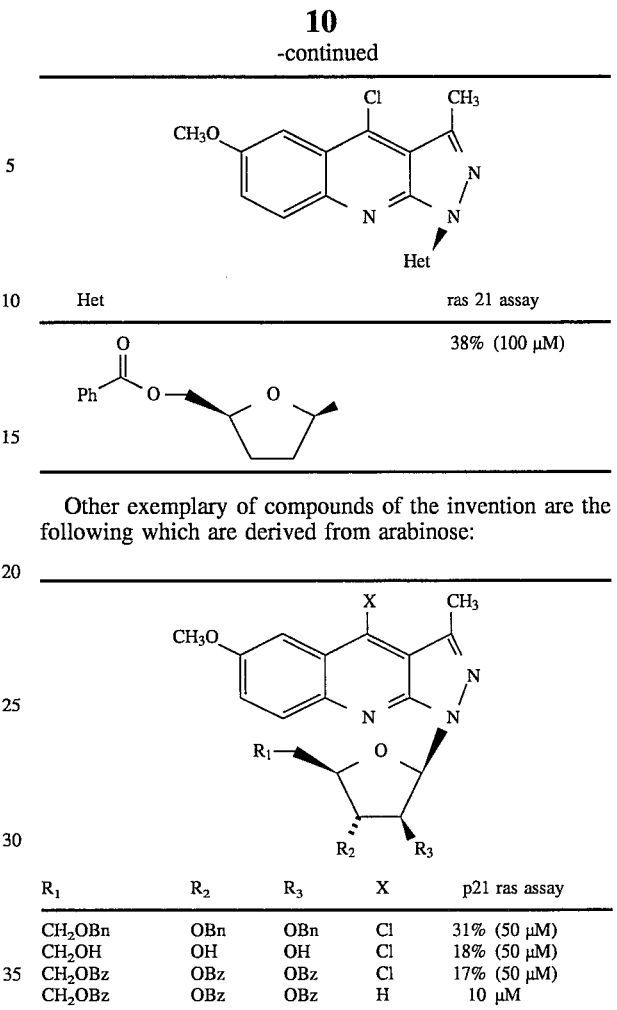

| R₁ | R₂ | R₃ | X | p21 ras assay |
|---|---|---|---|---|
| CH₂OBn | OBn | OBn | Cl | 31% (50 μM) |
| CH₂OH | OH | OH | Cl | 18% (50 μM) |
| CH₂OBz | OBz | OBz | Cl | 17% (50 μM) |
| CH₂OBz | OBz | OBz | H | 10 μM |

The most preferred compound of the invention is:

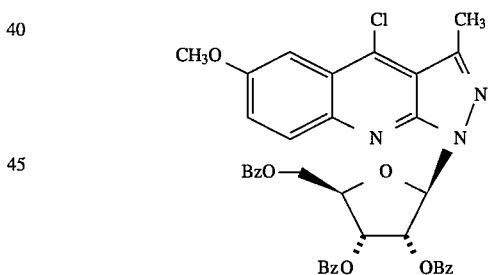

Compounds of the invention are active as agents in the treatment of tumors. Therefore, the present invention provides pharmaceutical compositions which comprise a compound of formula I: and a pharmaceutically acceptable carrier therefor which compositions are useful for treating patients afflicted with tumors. The present invention also provides methods of treating a patient having a tumor, which methods comprise administering to said patient an antitumor effective amount of a compound of formula I. The invention also relates to processes for preparing the compounds of the invention.

DETAILED DESCRIPTION OF THE INVENTION

The term "alkyl" refers to straight and branched chain hydrocarbon groups of 1 to 8 carbon atoms, such as methyl, ethyl, n-, and iso-propyl, n-, sec- and tert-butyl, n-, sec-, iso-, tert- and neo-pentyl, n-, sec- iso-, tert-hexyl and n-, sec-, iso-, tert-, and neo-heptyl and n-, sec-, iso-, tert-, and neo-octyl. The preferred $(C_1-C_8)$alkyl is methyl. Alternatively, alkyl with lower numbers of carbon atoms are also referred to in the specification. For example, the term "$(C_1-C_6)$alkyl" refers to straight and branched chain hydrocarbon groups of 1 to 6 carbon atoms, such as methyl, ethyl, n-, and iso-propyl.

The term "alkanoyl" refers to straight and branched chain alkanoyl groups having 1 to 8 carbon atoms such as formyl, acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, octanoyl, 2-ethylhexanoyl and the like. Alternatively, alkyl with lower numbers of carbon atoms may be referred to in the specification. For example, the term "$(C_1-C_3)$alkanoyl" refers to straight and branched chain alkanoyl groups of 1 to 3 carbon atoms.

As used herein, a boldfaced bond, ▬◀
denotes a bond which comes up out of the plane of the page. A dashed bond, ⅲⅰ
denotes a bond which comes down below of the plane of the page. A curved bond, ⟿
denotes a bond whose stereochemistry can either come up out of the plane of the page or down below of the plane of the page mixture.

As used herein, a curved line appearing next to a chemical moiety denotes the bond through which the moiety is attached to the rest of the molecule. Thus, for example, when $R_2$ and $R_3$ taken together are referred to as

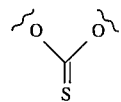

in conjunction with the

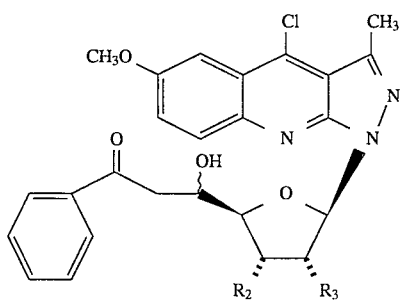

structure then the compound that is denoted is

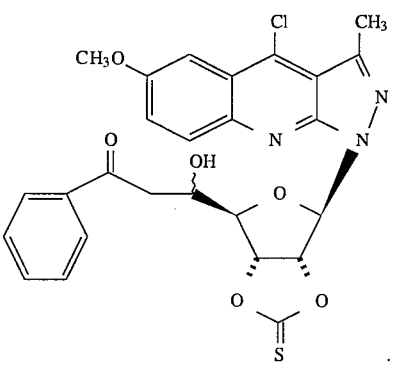

As used herein, the formula

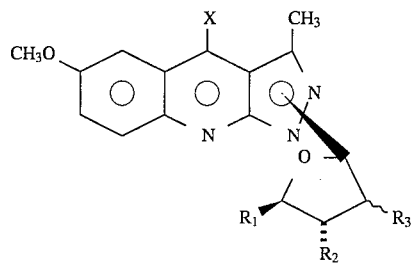

includes compounds of the formula

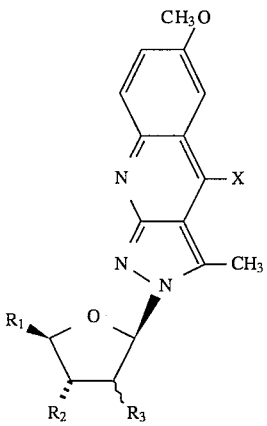

as well as compounds of the formula

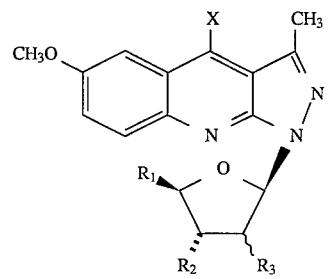

wherein X, $R_1$, $R_2$, and $R_3$ are as described herein.

As used herein, the compounds of formulas I and II wherein X is OH are understood as including the tautomeric keto-form. Thus, for example,

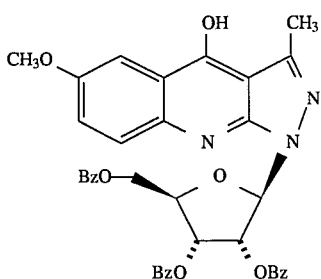

includes the tautomeric keto-form,

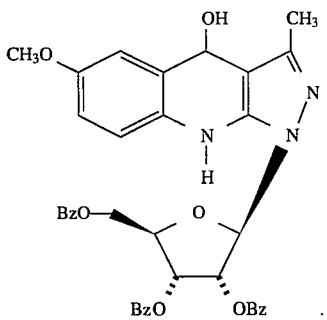

The term "pharmaceutically acceptable salt" refers to maleates, hydrochlorides, hydrobromides, sulfates, phosphates and tartrates. One skilled in the art will realize that acid addition salts of the compounds of the invention may be made with such salts whenever a basic functionality is present in a particular compound of the invention.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an antitumor effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antitumor activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to abut 100 mg/kg of body weight.

The dosage to be administered and the route of administration depends upon the particular compound used, the age and general health of the patient and the severity of the tumor condition. Thus, the dose ultimately decided upon must be left to the judgment of a trained health-care practitioner.

As noted above, certain compounds of the invention are also active as anti-tumor agents. These compounds may be administered by any conventional mode of administration by employing an antitumor effective amount of a compound of the invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Activity of the compounds of the invention may be demonstrated by the following assay.

Ras p21 Nucleotide Exchange Assay

The conditions for assay of nucleotide exchange inhibitors was adapted from Hall, A. and A. J. Self. 1986 J. Biol. Chem. 261: 10963–10965, which is hereby incorporated by reference.

0.5 µM ras p21 protein was incubated in 50 µls exhange buffer (50 mM Tris-HCl pH 7.5, 5 mM $MgCl_2$, 50 mM NaCl and 10 EDTA) on ice. Compounds dissolved in dimethyl sulfoxide (DMSO) were added to the desired concentration such that the final concentration of DMSO in the reaction mixture was 2% by weight. The reaction was incubated for 5 minutes on ice and then $^3$H-GDP (final concentration was 0.25 µM) was added. The reaction was further incubated for 30 minutes at 37° C. and then stopped by addition of excess cold buffer W (10 mM Tris-HCl pH 7.5, 10 mM $MgCl_2$ and 10 mM $NH_4Cl$. The ras p21 protein was collected on pure nitrocellulose filters (0.2µ pore size). The filters were washed extensively with cold buffer W and then allowed to air dry. Radioactivity on each filter was determined by scintillation counting. The amount of radioactivity bound to the filter is a direct measure of the amount of $^3$H-GDP bound to p21 ras. The extent to which a compound inhibited the exchange reaction was determined by comparing the amount of $^3$H-GDP bound to the protein in the presence of that compound versus the amount of $^3$H-GDP bound to the p21 ras in the absence of that compound.

Activity of the compounds of the invention in the assay set forth just above indicates that the compounds of the invention have activity as anti-tumor agents. More specifically, inhibition of the binding of $^3$H-GDP to the ras p21 protein by a compound, indicates that the compound has activity as an antitumor agent.

Biological data are given throughout the specification in one of two forms: either as per cent inhibitions, or as the concentration at which the test compound causes 50% inhibition ($IC_{50}$) of the binding of $^3$H-GDP to the p21 ras protein.

When the above assay was run at one concentration of the test compound, then the data was given as per cent inhibition at a particular concentration. An example of such a data point would be 44% (50 µM), which means 44% inhibition at a concentration of 50 µM. When the assay was run at a series of concentrations, then the data were given as $IC_{50}$'s.

Unless otherwise noted, all reactions were run under an inert atmosphere such nitrogen. Most chromatographies were started by dissolving the reaction residue in the more polar solvent to keep it homogeneous for loading.

What follows are a reaction scheme and examples showing how the compounds of the invention are made.

One of ordinary skill in the art may prepare all of the compounds of the invention by the examples and methods shown herein; or by methods analogous to those shown herein.

REACTION SCHEME 1

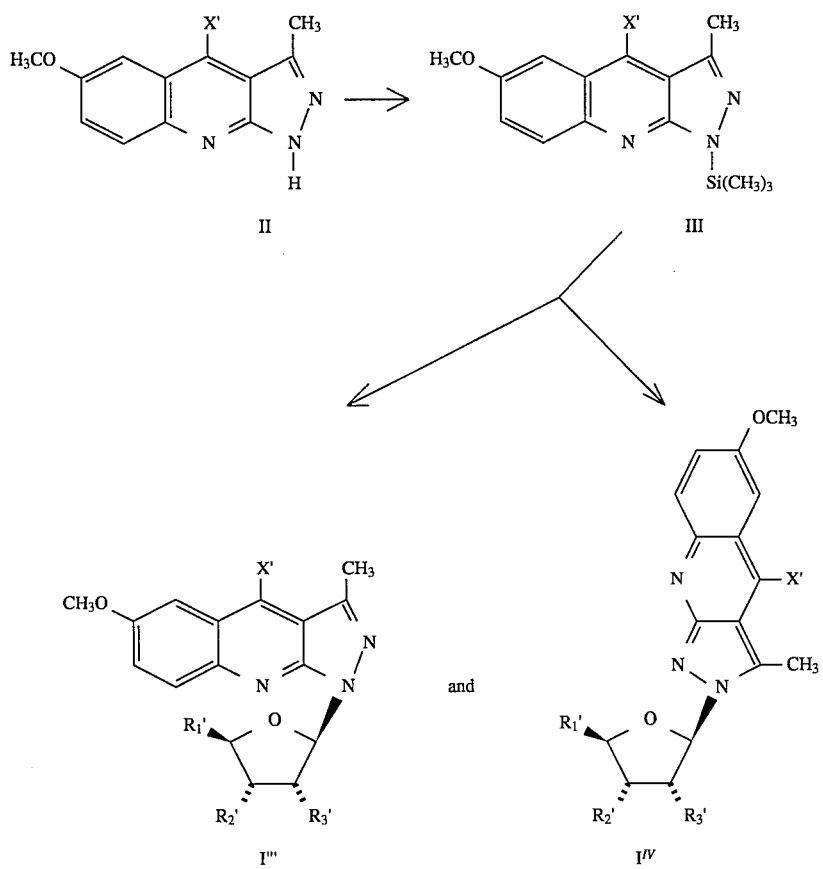

wherein X' is H or Cl, and $R_1'$ is $CH_3COOCH_2$ or $PhCOOCH_2$, $R_2'$, and $R_3'$ are each independently $CH_3COO$ or $PhCOO$.

In above REACTION SCHEME 1, when X is H in the compound of formula II, there is obtained a compound of formula III wherein X is also H. When X is Cl in the compound of formula II, there is obtained a compound of formula III wherein X is also Cl.

The compound of the formula

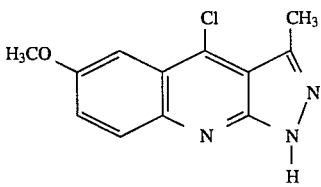

may be converted to the compound of the formula

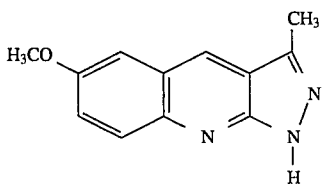

as described below. Of course, the two just above mentioned compounds are encompassed in formula II.

In above REACTION SCHEME 1, when X is H in the compound of formula III, there are obtained compounds of formulas I''' and $I^{IV}$ wherein X is also H. When X is Cl in the compound of formula there are obtained compounds of formulas I''' and $I^{IV}$ wherein X is also Cl.

The compound of the formula

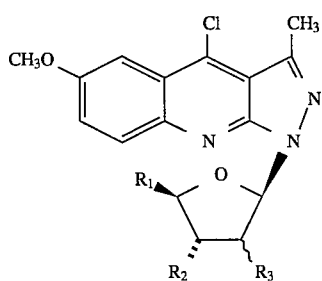

may be converted to the compound of the formula

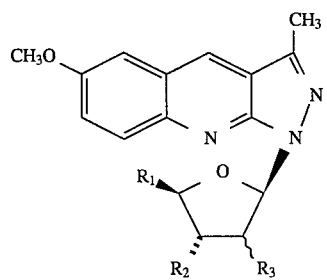

wherein $R_1$, $R_2$, and $R_3$ are as described herein. Of course, the two just above mentioned compounds are encompassed in formula I'.

As described below, compounds of formulas I' and I" in REACTION SCHEME 1 may be wholly or partially deprotected as described below, in order to obtain compounds wherein $R_1$ is either $CH_2OH$ or $CH_2OR_1$'; $R_2$ is either H or $R_2$'; and $R_3$ is either H or $R_3$', in all possible combinations.

A description of the reactions set forth in REACTION SCHEME 1 now follows. A compound of formula II may be reacted with a silylating reagent such as bistrimethylsilylacetamide (BSA) or more preferably trimethyl silyl diethylamine ($Et_2NTMS$) in an aprotic solvent such as methylene chloride, acetonitrile, or more preferably 1,2-dichloroethane under an inert atmosphere such as nitrogen or argon, at a temperature in the range of about 60° to about 80° C. most preferably about 100° C. for about 2 to about 4 hours, most preferably about 2.5 hours. Typically the reaction mixture begins as heterogeneous and by the end of the reaction it is homogeneous. The transformation of the reaction mixture from heterogeneous to homogeneous indicates that the silylation reaction is proceeding to completion.

At room temperature, the resulting TMS-intermediate (which is a compound of formula III) is redissolved in an aprotic solvent such as methylene chloride, acetonitrile or more preferably 1,2-dichloroethane to which is added a protected ribofuranose such as 1-acetate-2,3,5-ribosetribenzoate, followed by a Lewis acid catalyst such as $SnCl_4$ or more preferably, trimethylsilyltriflate (TMSOTf) at room temperature, then heated in the range of about 60° to about 80° C. more preferably about 80° C. The reaction mixture is then cooled to room temperature whereupon conventional workup results in a mixture of compounds of formula I' and I".

The compound of formula II wherein X' is Cl may be prepared in accordance with methods set forth in copending application Ser. No.08/234,742 filed Apr. 28, 1994 which is hereby incorporated by reference. The compound of formula II wherein X' is H may be prepared in accordance with methods set forth herein.

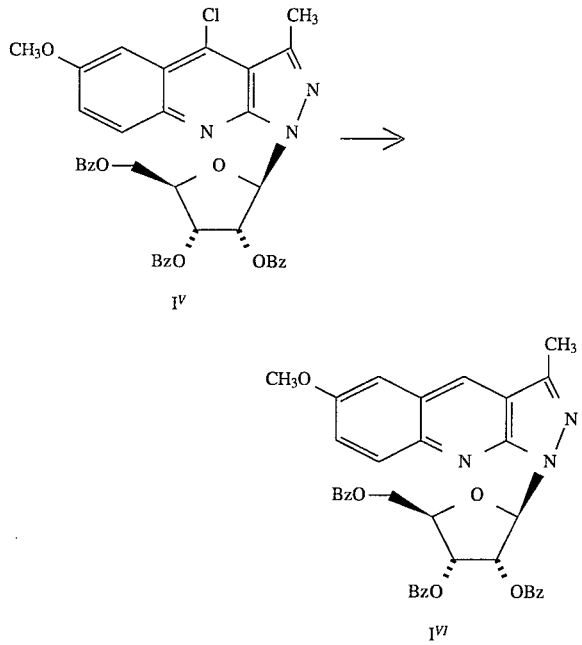

A compound of formula $I^V$ may be reacted with a hydrogenation catalyst such as 10% Pd/C or more preferably Pd black, and further with a hydogen transfer source such as cyclohexene or more preferably cyclohexadiene in a polar solvent such as DMF or ETCH, more preferably, ETCH. The reaction flask is fitted with a reflux condenser with an empty balloon placed at the top so that when hydrogen evolution takes place, the balloon fills with hydrogen so as to maintain a hydrogen atmosphere over the reaction. The Pd black and cyclohexadiene are added at room temperature The reaction is heated in a range of about 60° C. to about 80° C. most preferably about 60° C. for about 2 hours or until complete as shown by tlc (thin layer chromatography). Conventional workup will yield a compound of formula $I^{VI}$.

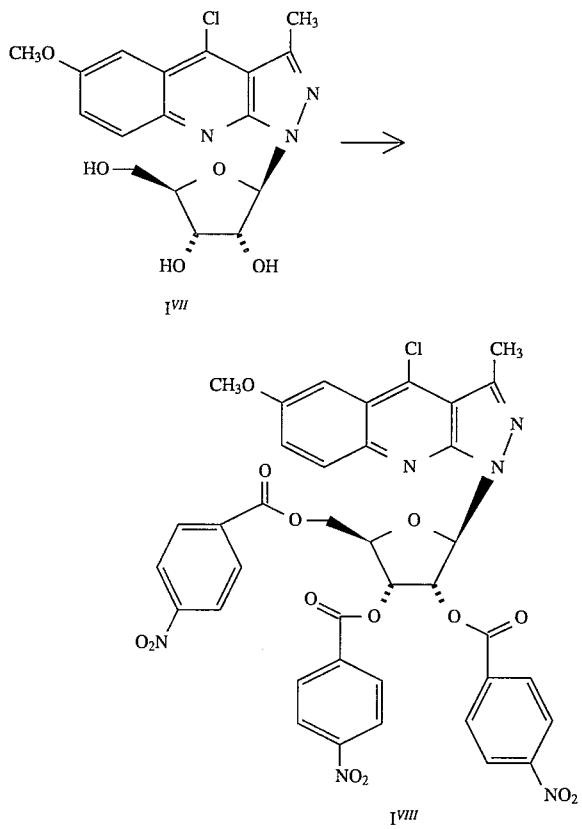

A compound of formula $I^{VII}$ may be reacted with p-nitrobenzoyl chloride in a basic solvent such as pyridine (most preferred) triethylamine also containing an acetylating catalyst such as dimethyl amino pyridine (DMAP). These materials are added at 0°–25° C. and then the reaction mixture is heated to 80°–115° C. preferably 100° C. for about 2 to 4 hours, most preferably about 3 hours. The solvent is evaporated, and the residue is chromatographed directly on silica gel using a slightly polar solvent such as 2% Et OAc-Hexane to obtain a compound of formula $I^{VIII}$.

One of ordinary skill in the art may prepare compounds of formula I of the invention having all possible esters or combinations of esters and hydroxy groups described herein, by methods shown herein; or by methods analogous to those shown herein; or by known literature methods. For example, the acid chloride used in the above reaction may be an acid chloride such as a substituted benzoyl chloride which contains methoxy, nitro, methyl, or acetyl as the substituents. Nitro as the substituent is most preferred.

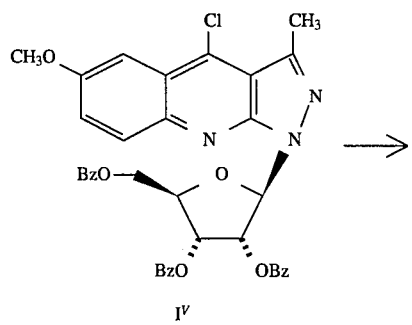

I<sup>V</sup>

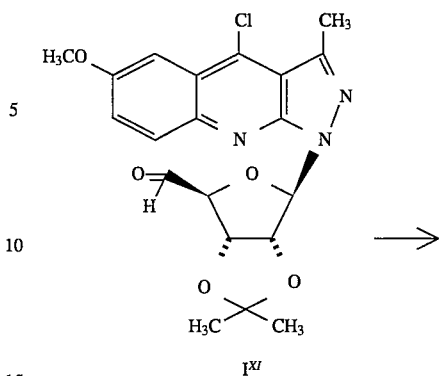

I<sup>XI</sup>

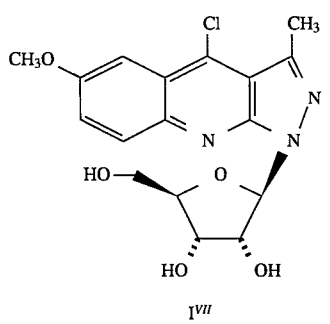

I<sup>IX</sup>

AND

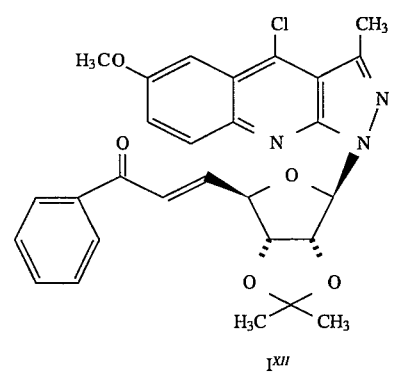

I<sup>XII</sup>

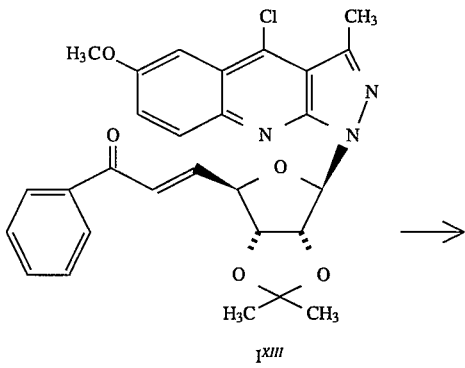

I<sup>VII</sup>

A compound of formula I$^V$ may be reacted with a deprotecting base such as NaOMe in the polar, protic solvent MeOH. Alternatively, as the solvent, MeOH may be used with enough CH$_2$Cl$_2$ to afford a homogenous solution. The reaction is run at room temperature. An equivalent weight of SiO$_2$ is added to the reaction mixture and the resulting material is evaporated to dryness. This material is then poured on top of silica gel column and eluted to obtain a compound of formula I$^{IX}$.

If it is desired to obtain a mixture of compounds of formulas I$^{IX}$ and I$^{VII}$, then rather than using NaOMe as the deprotecting base, one may use methanolic ammonia. The resulting mixture may be separated by chromatography.

These deprotection reactions can also be run on the N-2 isomer.

The compound of formula I$^{XI}$ may be reacted with a homologation reagent such as the Emmons Horner reagent or more preferably a Wittig reagent such as 2,2,2-triphenylacetylphenone in a polar, aprotic solvent such as dioxane, acetonitrile, or more preferably THF at a temperature in the range of about room temperature to about 100° C. most preferably about 60° for about 6 to about 48 hours. Evaporation of the solvent and chromatography of the residue will yield a compound of formula I$^{XII}$.

I$^{XIII}$

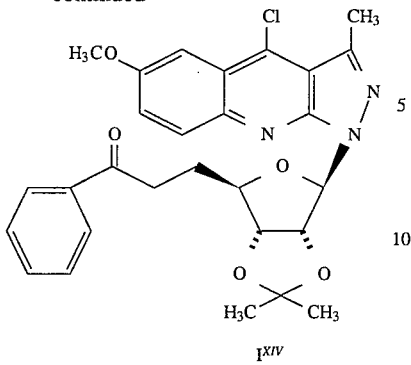

I$^{XIV}$

A compound of formula I$^X$ may be reacted with a hydogenating catalyst such as Pd/C, Pd(OH)$_2$ or more preferably hydrogen in the presence of PtO$_2$ in a polar solvent such as methanol or ethanol or more preferably methanol/ethyl acetate (1:5) at a temperature in the range of about room temperature to about 80° C. most preferably about 60° C. for about 10 minutes to about 2 hours, more preferably about 25. Conventional isolation, which includes filtration of the hydrogen catalyst followed by evaporation of the solvent will yield a compound of formula I$^{XI}$.

This hydrogenation reaction is applicable to other compounds of formula I of the invention. One skilled in the art would note that certain substituents are not stable in the presence of a hydogenating agent. In such cases, these substituents would be protected, the hydogenation reaction would be carried out, then the substituents would be deprotected The invention disclosed herein is exemplified by the following preparative examples, which should not be construed to limit the scope of the disclosure. Alternative mechanistic pathways and analogous structures within the scope of the invention may be apparent to those skilled in the art.

EXAMPLES

Example 1

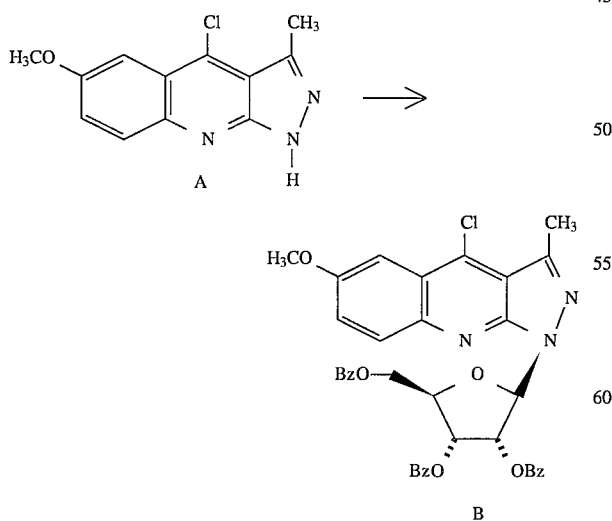

B
and

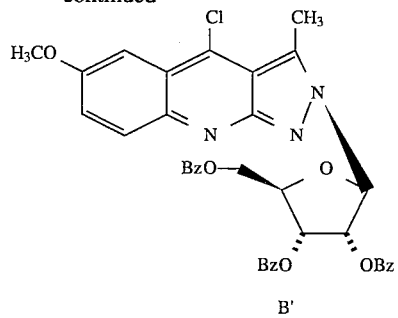

B'

Procedure for Ribosilylation w/pyrazoloquinolines:

Example for Compound B: To a heterogeneous solution of compound A (11.2 g, 45.3 mmol) in 1,2-dichloroethane (150 mL) was added Et$_2$NTMS (15 mL, 11.5 g, 79.3 mmol) under a nitrogen atmosphere at room temperature. The mixture was heated to 80° C. for about 2.5 hours affording a homogeneous solution. After cooling to room temperature the solvent was evaporated under reduced pressure to give the silylated base as a yellowish solid. The TMS-intermediate was redissolved in 1,2-dichloroethane (150 mL) to which was added 1-acetate-2,3,5-ribosetribenzoate (25.14 g, 49.8 mmol), followed by TMSOTf (12.2 g, 10 mL, 54.8 mmol) at room temperature. The mixture was heated to 80° C. for 4 hours then cooled to room temperature and poured into a saturated solution of NaHCO$_3$ at 0° C. with stirring for 15 minutes. The aqueous portion was extracted repeatedly with CHCl$_3$, and the combined organics were washed with brine, dried over Na$_2$SO$_4$, filtered and concentrated under reduced pressure. Chromatography on SiO$_2$ using (CH$_2$C$_2$:EtOAc:Hexane, 3:17:80 increasing CH$_2$Cl$_2$ gradually) provided 18.8 g (60%) of compound, B, as a light yellow solid. 825 mg of compound Analytical data for compound B is, MS (Cl, M+1)=692, mp=85°–115° C.

Analytical data for compound B' is, MS (Cl, M+1)=692.

Example 2

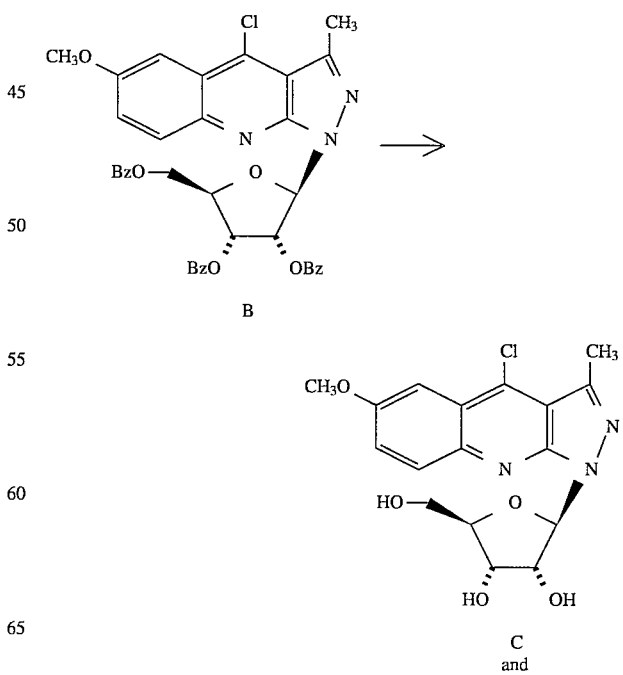

C
and

-continued

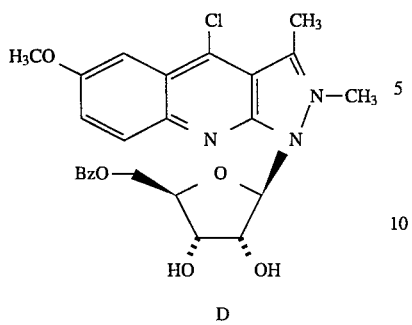

D

Procedure for hydrolysis w/ammonia:

Example for Compounds C and D: To compound B was added a saturated solution of methanolic ammonia. The mixture was stirred at room temperature for 3 days in a stoppered flask. $SiO_2$ was then added to the mixture and the solvent was evaporated under reduced pressure. Purification by flash chromatography on $SiO_2$ (MeOH—$CH_2Cl_2$) provided the $C_5'$-monobenzoate, compound D and the triol, compound C in ratios that varied from experiment to experiment. Use of NaOMe as shown in Example 3 below, provided only the triol compound C.

Analytical data for compound D (Cl, M+1)=484, MP=230–232, Calc. C, 59.57; H, 4.58; N, 8.68. Found, C, 59.68; H, 4.56; N, 8.64.

Analytical data for compound C, MS (Cl, M+1)=380, MP=198–200, Calc. C, 53.76; H, 4.78; N, 11.06; Cl, 9.33. Found C, 53.67; H, 4.69; N, 10.83; Cl, 9.19.

Example 3

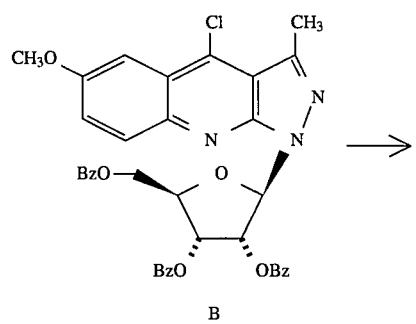

B

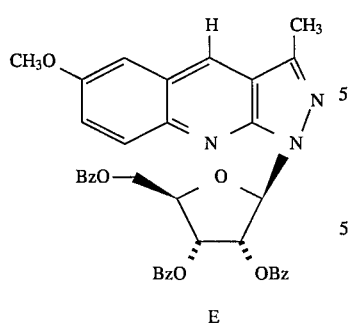

E

Example for Compound C Compound B (18.8 g, 27.2 mmol) was dissolved in MeOH (400 mL) and just enough $CH_2Cl_2$ (50 mL) to afford a homogenous solution. NaOMe (5.8 g, 107 mmol) was added and the mixture was stirred at room temperature for 3 hours, $SiO_2$ (20 g) was added to the reaction mixture and then evaporated to dryness under reduced pressure. The adsorbed product was then chromatographed on $SiO_2$ using (5% MeOH:$CH_2Cl_2$) which afforded 8.45 g (82%) of compound C.

Example 4

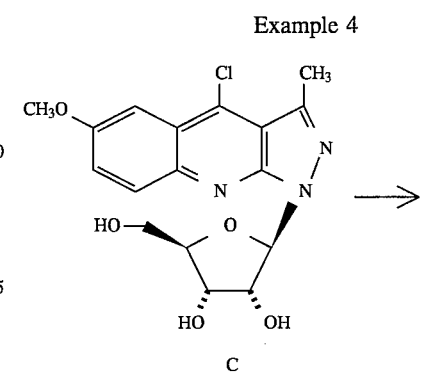

C

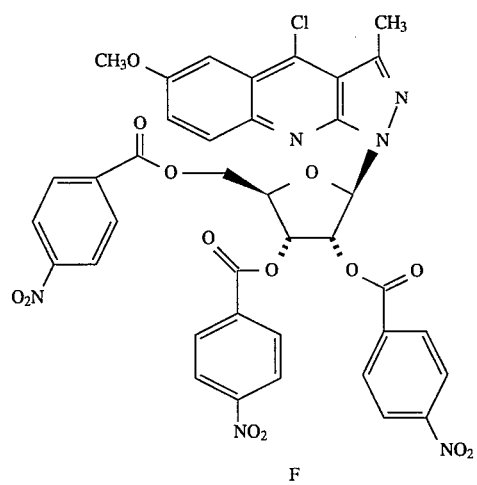

F

Procedure for preparation of the triesters w/pyrazoloquinolines:

Example for Compound F: To a pyridine solution (50 mL) of compound C (500 mg, 1.59 mmol) was added p-nitrobenzoyl chloride (1.77 g, 9.54 mmol) and DMAP (50 mg, 0.410 mmol) at room temperature The mixture was heated to 100° C. under a nitrogen atmosphere for 3 hours, then the solvent was removed under reduced pressure and the crude product was chromatographed on $SiO_2$ (2% EtOAc-Hexane) affording 1.06 g (80%) of the ribosetriester compound F.

Analytical data, MS (Cl, M+1)=534, Calc. C, 58.54; H, 3.59; N, 7.88. Found, C, 58.65; H, 3.88; N, 7.64.

Example 5

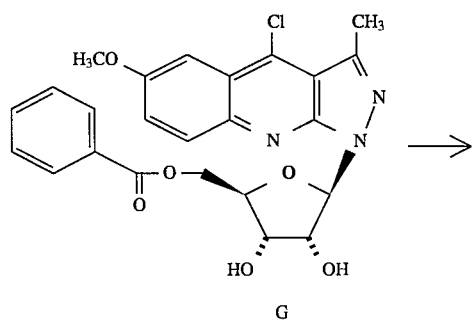

G

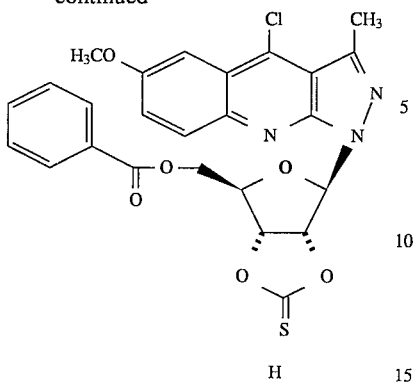

Conversion of Compound G to the dihydrofuran compound H:

To a heterogeneous 1,2-dichloroethane solution of compound G (700 mg, 1.45 mmol) was added thiocarbonyl diimidazole 400 mg, 2.24 mmo) at room temperature. The mixture was heated to 80° C. and after 2 hours a homogeneous yellow homogeneous solution resulted. After an additional 2 hours at 80° C., the solvent was removed and the residue was chromatographed on SiO$_2$ (2% actone-CH$_2$Cl$_2$) which gave the 550 mg (72%) of the thiocarbonate compound H as a yellow solid and 120 mg of recovered starting material. Tet. Lett., vol. 23, no. 19, pp 1979–1982 (1982) JACS Vol. 87, No. 4 (1965) pp934.

Analytical data for compound H, MS (Cl, M+1)=526.

Example 6

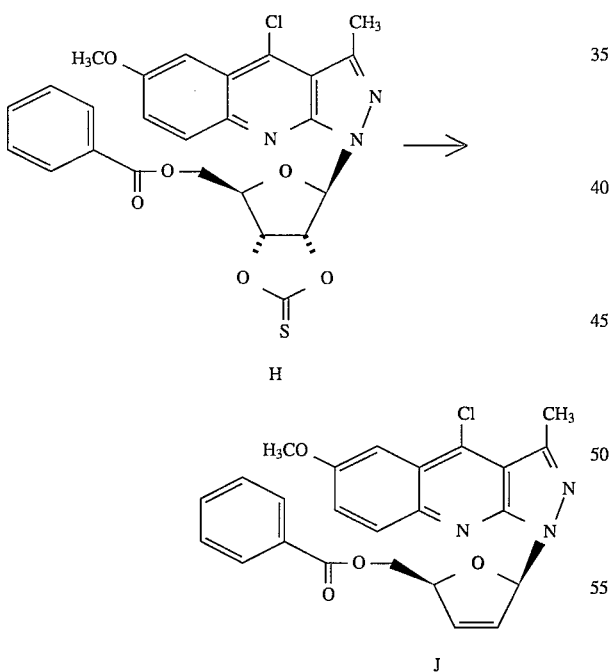

Conversion of Compound H to the olefin Compound J: 51830 to 51856

Sch 51830 (550 mg, 1.04 mmol) was dissolved in neat (MeO)$_3$P (8 mL) and the mixture was heated to 120° C. After 1 hour a homogeneous solution resulted, and after 4 hours the reaction was judged to be complete by tlc. After cooling to room temperature the (MeO)$_3$P was removed under reduced pressure employing a series of two dry ice-acetone traps. The residue was taken up in CH$_2$Cl$_2$ and chromatographed initially on SiO$_2$ (1% MeOH—CH$_2$Cl$_2$) and then again using (20% acetone-hexane increasing gradually to 30% acetone-hexane) which gave 461 mg (98%) of the dihydrofuran, compound J as a bright yellow solid.

Analytical data for compound J, mp=144–147.

Example 7

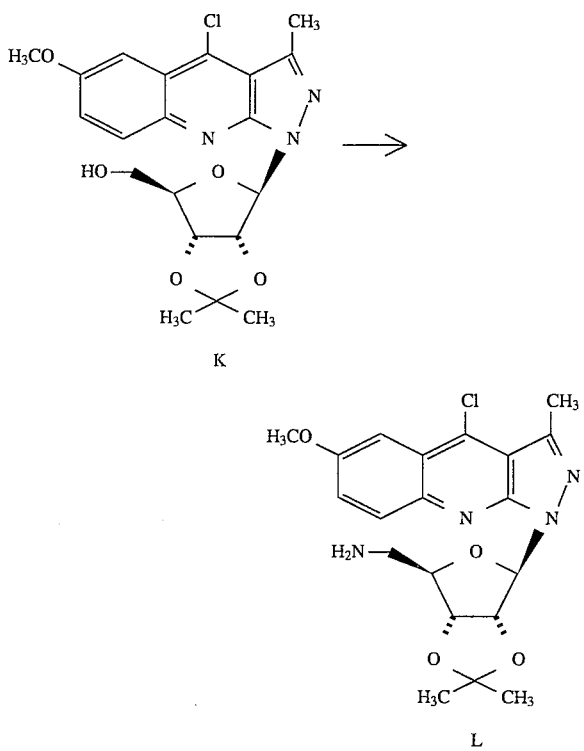

Conversion of Compound K to Compound L

A flask containing compound K (200 mg, 0.477 mmol) in THF (4 mL) was added Ph$_3$P (210 mg, 0.764 mmol) and diethylazodicarboxylate (DEAD) (134 mg, 0.772 mmol) at room temperature followed by the dropwise addition of diphenylphosphoryl azide (230 mg, 0.836 mmol). The reaction mixture was allowed to stir at room temperature for 24 hours, and the solvent was removed under reduced pressure. Chromatography of the oily residue on SiO$_2$ (10% acetone-hexane) gave the azide as a yellowish-green solid, which was unstable at room temperature and light. Reduction of the azide to the amine was best accomplished using Ph$_3$P in a THF/H$_2$O solution at room temperature for 48 hours. After chromatography on SiO$_2$ (2% MeOH—CH$_2$Cl$_2$ increasing gradually to 5% MeOH—CH$_2$Cl$_2$) 92 mg (46% after 2 steps) of compound L was obtained. Yamada et al, JACS, 6203 (1972).

Analytical data for compound L, MS (Cl, M+1)=419.

The first step of the above reaction is the formation of an azide which can be carried out by conventional procedures including reaction with an azide forming reagent. The second step of this reaction is the reduction of the azide to the amine which can be accomplished through hydrogenation, or more preferably a reducing agent such as Ph$_3$P, in a solvent such as aqueous THF, aqueous dioxane, or aqueous CH$_3$CN. Conventional workup will yield a compound L.

Example 8

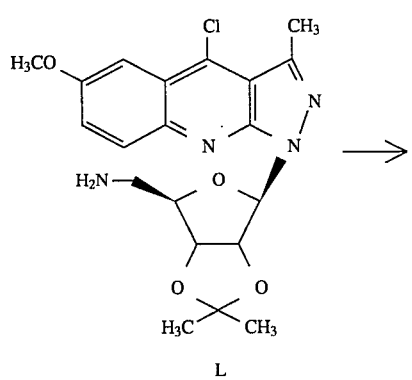

L

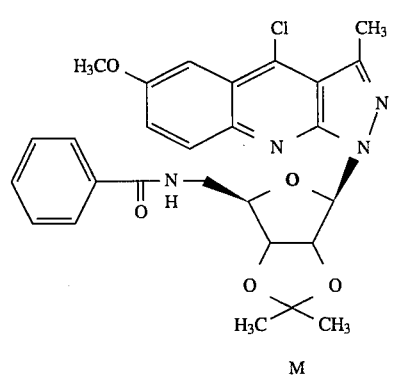

M

Preparation of the benzamide compound M

To compound L (250 mg, 0.598 mmol) in CH$_2$Cl$_2$ (8 mL) was added benzoic acid (100 mg, 0.819 mmol), DCC (200 mg, 0.971 mmol), and DMAP (10 mg, 0.082 mmol) at room temperature. A heterogeneous mixture resulted after approximately 5 minutes and stirring was continued for an additional 3 hours. The contents were concentrated in vacuo and chromatographed on SiO$_2$ (3% acetone-CH$_2$Cl$_2$) which afforded the benzamide contaminated with residual Ph$_3$P. Repeated recrystallization of this material from Et$_2$O afforded 198 mg (63%) of compound M as a pale off white solid.

Analytical data for compound M, MS (Cl, M+1)=523.

This reaction was performed in accordance with JACS 1958) 6204 and "Greene and Protective Groups in Organic Synthesis" 2nd Edition. Greene and Wuts. John Wiley & Sons, Inc., (1991), which are hereby incorporated by reference.

Example 9

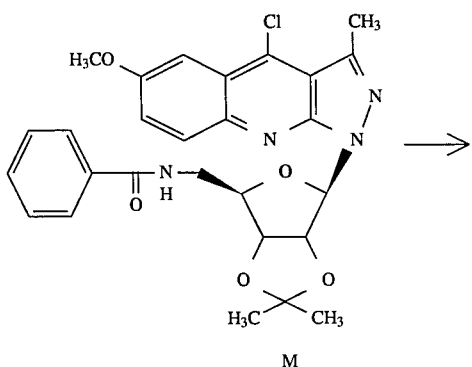

M

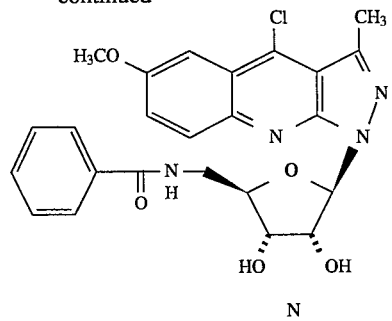

N

Hydrolysis of compound M to compound N:

Compound M (130 mg, 0.249 mmol) was dissolved in a THF—MeOH—H$_2$O (6:2:1) solution, to which was added 3M HCl. A bright yellow solution resulted which was heated to 45° C. for 7 hours. The contents were cooled to room temperature and evaporated under reduced pressure yielding a bright yellow solid. Chromatography on SiO$_2$ (3% MeOH—CH$_2$Cl$_2$ increasing to 5% MeOH—CH$_2$Cl$_2$) provided 66 mg (55%) of the diol, Compound N, as a bright yellow solid.

Analytical data for Compound N is: MS (Cl, M+1)=483.

Example 10

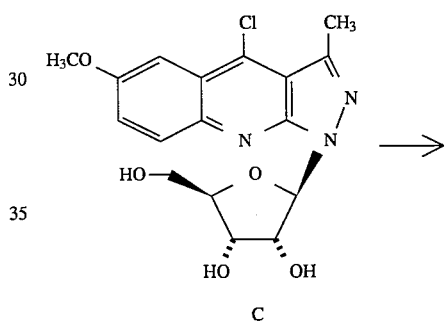

C

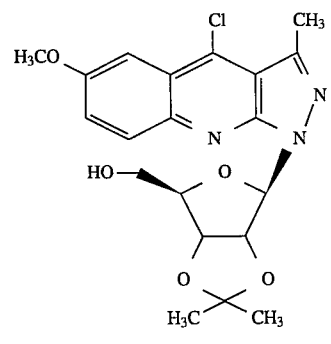

K

Preparation of compound K—Acetonide formation:

To a DMF solution (1.5 mL) of compound C (470 mg, 1.24 mol) was added 2,2-dimethoxypropane (5 mL) followed by p-toluenesulfonic acid (p-TsOH) (10 mg) at room temperature. After stirring the mixture at room temperature overnight, the solvent was evaporated under reduced pressure and the viscous residue was diluted with CHCl$_3$ and chromatographed on SiO$_2$ using (15% EtOAc-Hexane) to give 415 mg (79%) of compound K as a yellow amorphous solid.

Analytical data for compound K is: MS (Cl, M+1)=420, Calc. C, 57.21; H, 5.28; N, 10.00. Found, C, 57.14; H, 5.28; N, 9.73.

Example 11

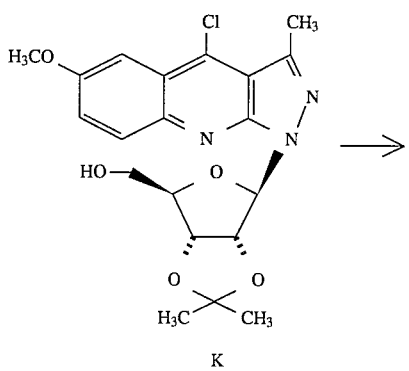

K

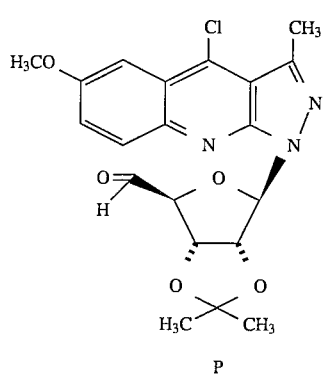

P

Procedure for Moffatt oxidation to the C5' aldehyde in the ribose series: Example for Compound P:

To a flask containing compound K (2.47 g, 5.89 mmol) was added DMSO (60 mL) followed by dicyclohexylcarbodiimide (DCC) (5.03 g, 24.4 mmol) and dichloroacetic acid (0.30 mL, 3.7 mmol) at room temperature. After stirring for 30 hours, the contents were diluted with H$_2$O and extracted with CH$_2$Cl$_2$. The combined organics were washed with brine, dried over Na$_2$SO$_4$, filtered and concentrated. Chromatography on SiO$_2$ using (3% EtOAc—CH$_2$Cl$_2$) afforded 2.11 g (85%) of the aldehyde, compound P.

Analytical data for compound P is: MS (Cl, M+1)=418.

This reaction was performed in accordance with the procedures set forth in J. G. Moffatt, J. Org. Chem., 1909, (1971) which is hereby incorporated by reference.

Example 12

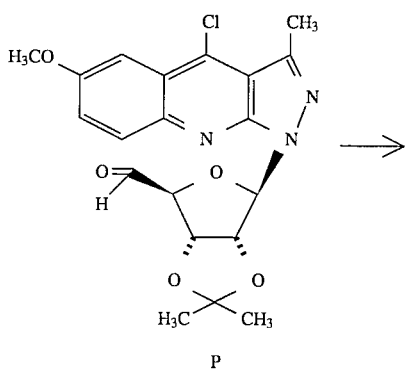

P

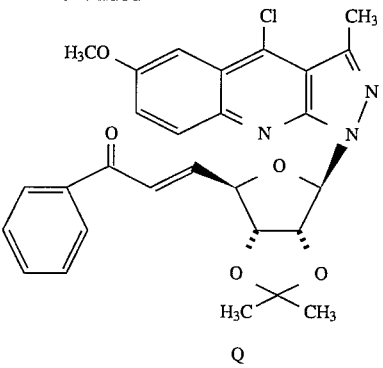

Q

Procedure for Wittig homologation:

Example for Compound Q: To compound P (2.51 g, 6.02 mmol) in THF (100 mL) was added 2,2,2-triphenylacetylphenone (3.43 g, 9.03 mmol) at room temperature and the mixture was allowed to stir at 60° C. for 20 hours. The solvent was then evaporated under reduced pressure and the residue was chromatographed on SiO$_2$ using (2% EtOAc—CH$_2$Cl$_2$) which provided 2.65 g (84%) of compound Q.

Analytical data for compound Q, MP=106–113. MS (Cl, M+1)=520.

Example 13

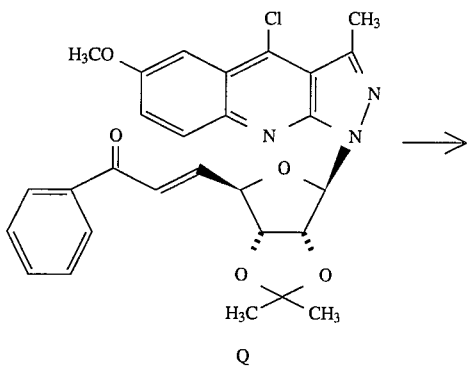

Q

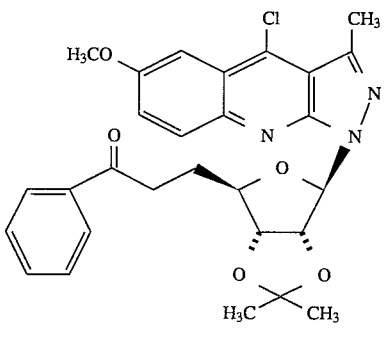

R

Hydrogenation of C=C bond:

Example for compound R: To an EtOH—EtOAc (4:10 v/v) solution of compound Q (0.500 g, 0.963 mmol) was added PtO$_2$ (0.20 g) followed by charging the flask with hydrogen from a balloon. After 25 minutes the reaction was judged to be complete by tlc. The catalyst was removed by filtering through celite and the effluent was concentrated under reduced pressure. Chromatography of SiO$_2$ using (2%

EtOH—CH$_2$Cl$_2$) afforded 0.285 g (57%) of the saturated ketone, compound R.

Analytical data for compound R is: MS (Cl, M+1)=522.

Example 14

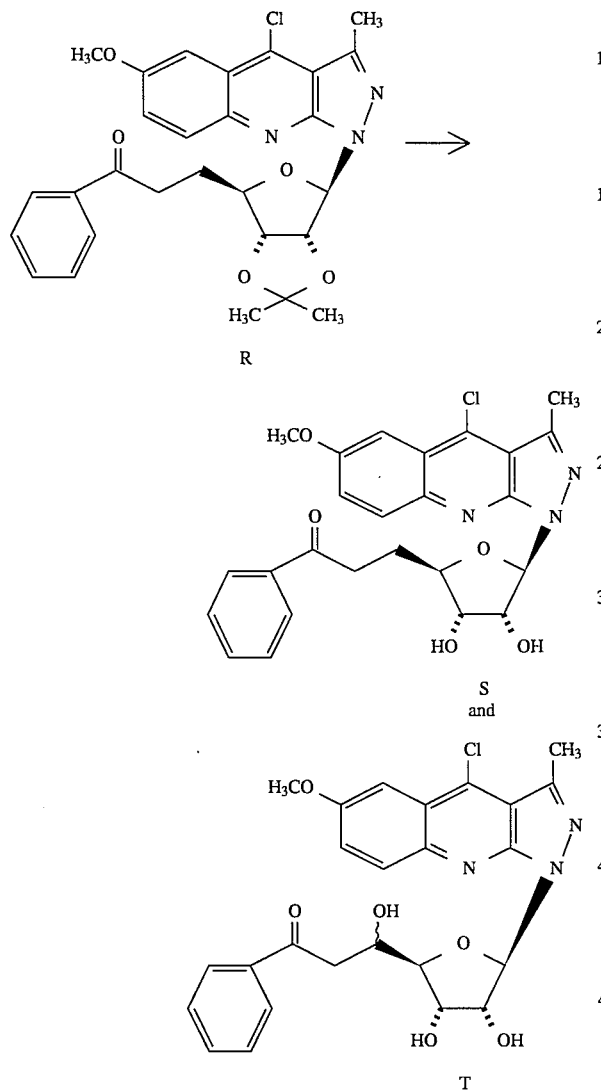

Procedure for the deprotection of the acetonide:

Example for Compound S To compound R (1.31 g, 2.51 mmol) in THF (100 mL) was added 1N HCl (100 mL) at room temperature. The reaction was heated to 60° C. for 20 hours, and then at reflux for 6 hours. When the reaction was judged to be complete by tlc, the mixture was cooled to room temperature diluted with H$_2$O and extracted with CH$_2$Cl$_2$. The organic portions were washed with brine, dried over Na$_2$SO$_4$, filtered and concentrated in vacuo to provide 755 mg (62%) fo the diol, compound S, and 269 mg (22%) of the triol, compound T.

The above reaction was carried out in accordance with the following publication: "Protective Groups in Organic Synthesis" 2nd Edition. Greene and Wuts. John Wiley & Sons, Inc., (1991), which is hereby incorporated by reference.

Analytical data for compound S is as follows: MS (Cl, M+1)=482. Data for compound T is: MS (Cl, M+1)=498.

Example 15

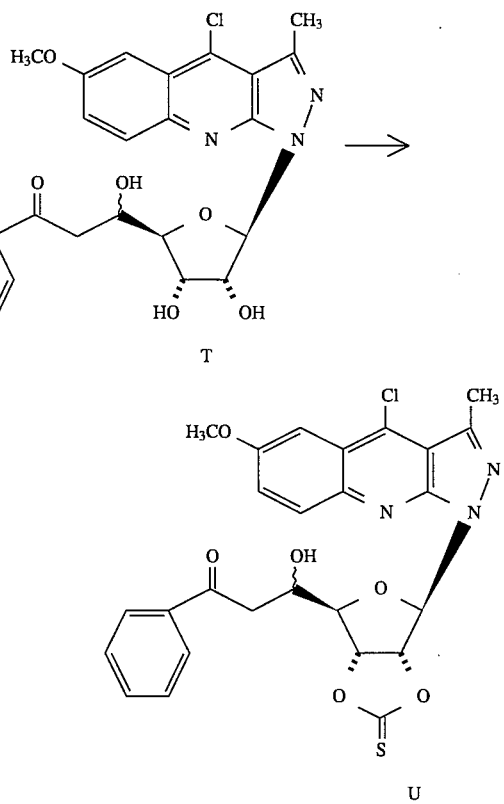

Procedure for formation of the thiocarbonate:

Example for Compound U: To a 1,2-dichloroethane solution (75 mL) of compound T (760 mg, 1.53 mmol) was added thiocarbonyldiimidazole (320 mg, 1.79 mmol) and the mixture was heated to reflux for 2 hours. The solvent was removed in vacuo and the crude yellow residue was chromatographed on SiO$_2$ using (2% acetone-CH$_2$Cl$_2$) to give 320 mg (41%) of compound U.

Analytical data for compound U is: mp 196-199 dec. MS (Cl, M+1)=540. In ras p21 assay, this compound had an IC$_{50}$ of 1.5 µM.

Example 16

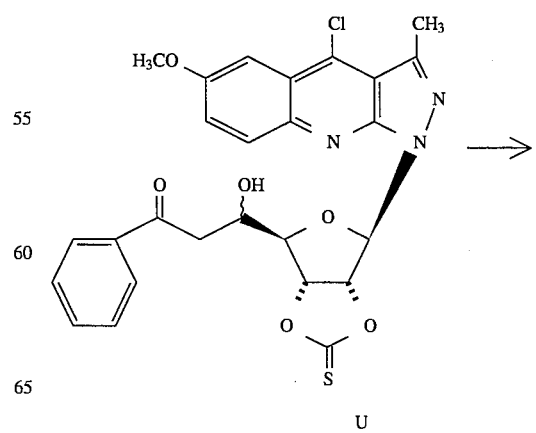

-continued

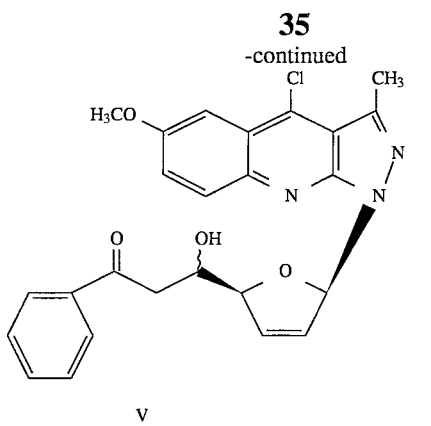

V

Procedure for the Corey-Winter Reaction:

Example for Compound V: Compound U (265 mg, 0.492 mmol) was dissolved in neat $(CH_3O)_3P$ (6 mL) and heated to 125° C. in an oil bath for 16 hours. The $(CH_3O)_3P$ was removed by evaporating under reduced pressure using a series of $CO_2$-acetone traps. The residue was chromatographed on $SiO_2$ using (20% acetone-hexane) which afforded 160 mg (72%) of Compound V as a bright yellow solid.

Analytical data for compound V is: MS (CI, M+1)=464.

Example 17

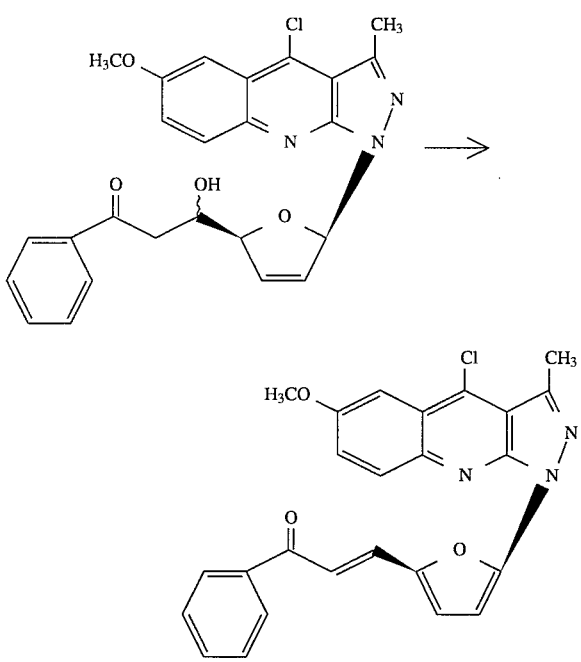

increasing gradually to (3% EtOAc-1% $CH_3CN$—$CH_2Cl_2$) gave 30 mg (62%) of compound W as a bright yellow solid.

Analytical data for compound W is: MS (CI, M+1)=445.

Preparation of the 1-Chloro-2.3.5-TriO-benzyl-D-arabinofuranose is described in J. Med. Chem. 526 (1992) and in Nucleic Acid Res, 1217 (1987) both of which references are hereby incorporated by reference.

Example 18

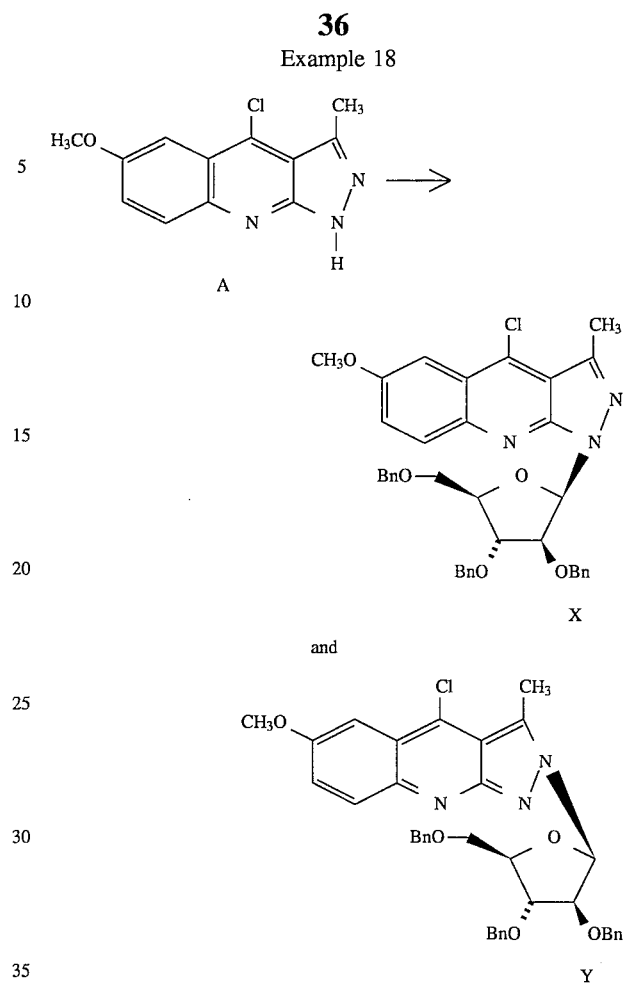

Arabinose condensation: Sodium hydride (100 mg, 2.50 mmol, 60% in oil) was added to a suspension of the pyrazoloquinoline A (500 mg, 2.0 mmol) in DMF (10 mL) at 20° C. After stirring for 0.5 hour, the arabinofuranose (1 g, 2.28 mmol) was added and the mixture was stirred at 60° C. for 2 hours. The solvent was evaporated and the residue was extracted with methylene chloride (120 mL). The organics were washed with water and dried over $MgSO_4$, filtered and concentrated to give an oil which was chromatographed on $SiO_2$ (10% ethyl acetate hexane. Two products were obtained: compound X (800 mg, 60%) compound Y (230 mg, 17%).

Analytical data for compound X is as follows: MS(FAB, M+1)=650.4, Analytical data for compound Y is as follows: MS(FAB, M+1)=650.3.

All of the chemistry which is done on a ribose containing molecule can be done on an arabinose containing molecule except for reactions like which require both hydroxy groups to be on the same face of the molecule in the final product. An example of such a reaction would be thiocarbonate formation.

Example 19

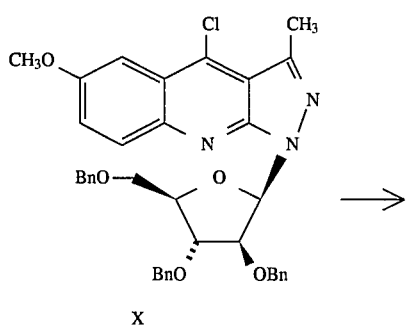

X

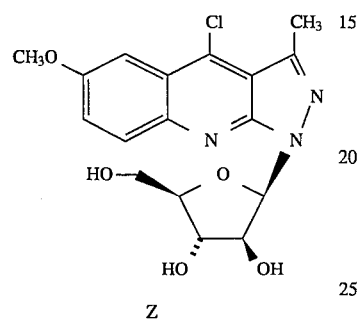

Z and

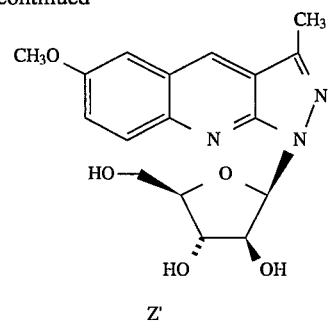

Z'

Benzyl deprotection of arabinose. Palladium black (30mg) and 1,4-cyclohexadiene (1.0 mL) was added to a solution of the tribenzyl ether which is compound X, (100 mg, $1.53 \times 10^{-4}$M) in DMF at 20° C. The mixture was stirred at 40° C. for 30 minutes. The reaction mixture was filtered through a Celite pad and the effluent was evaporated. A mixture of compounds Z and Z' (1:2) was obtained from the column (25 mg) and used in the reaction with benzoyl chloride, which appears in the next example.

Example 20

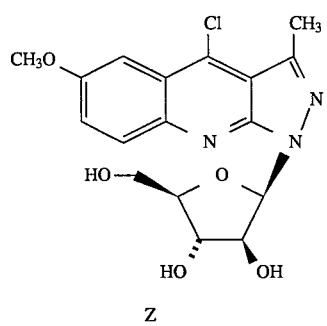

Z and

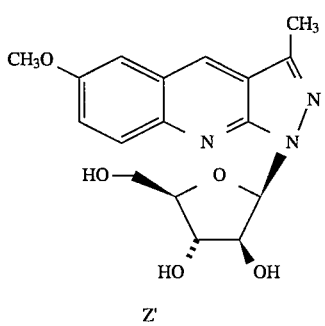

Z'

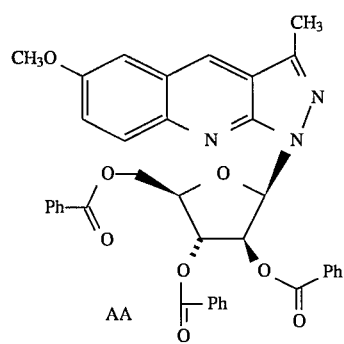

AA and

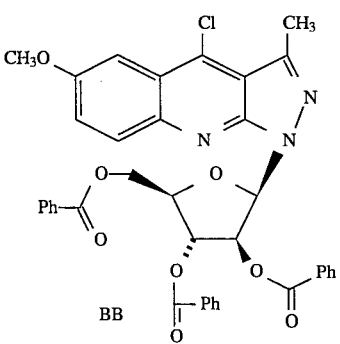

BB

Benzoylation. To a pyridine solution of a mixture of compounds Z and Z' (1:2) (50 mg) was added dimethylaminopyridine (5 mg) and benzoyl chloride (200 μl) at room temperature. The mixture was heated to 60° C. for 3 hours. The solvent was then evaporated and the residue was diluted with water and extracted with methylene chloride. The organics were dried over $MgSO_4$, filtered and concentrated to give an oil which was chromatographed on $SiO_2$ (15% EtOAc-Hexane) to afford two products, 25 mg of compound BB as a pale yellow solid and 45 mg of compound AA as a white foam.

Analytical data for compound BB is as follows: MS(FAB, M+1)=692. Analytical data for compound AA is as follows:, MS(FAB,M+1)=658.

Example 21

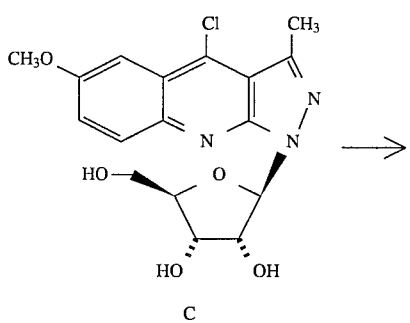

C

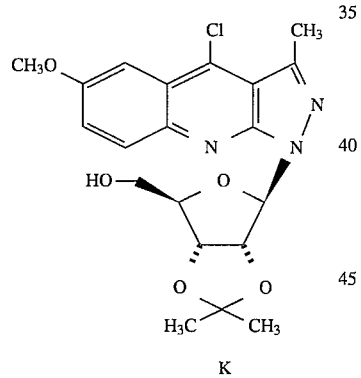

K

Preparation of compound K.-Acetonide formation: To a DMF solution (1.5 mL) of compound C, (4.70 mg, 1.24 mol) was added 2,2-dimethoxy propane (5 mL) followed by p-TsOH (10 mg) at room temperature. After stirring the mixture at room temperature overnight, the solvent was evaporated under reduced pressure and the viscous residue was diluted with $CHCl_3$ and chromatographed on $SiO_2$ using (15% EtOAc-HexanE) to give 415 mg (79%) of compound K as a yellow amorphous solid. The analytical data for compound compound K is:

MS (Cl, M+1)=420, Calc. 57.21; H 5.28; N 10.00. Found C, 57.14; H, 5.28; N, 9.73.

Example 22

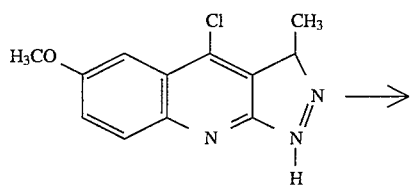

A

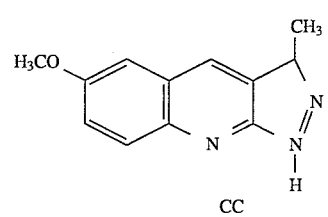

CC

To a heterogeneous solution of compound A (5.0 g, 20.1 mmol) in DMF (20 mL) and EtOH (10 mL) was added 1,4-cyclohexadiene (15 mL) followed by Pd black (2.7 g) at room temperature. The mixture was then raised to 80° C. using an oil bath. After about 1 hour, the palladium began to settle out and the reaction mixture became yellowish in color. After 3 hours all the palladium had settled out and a clear homogeneous solution resulted. Analysis of an aliquot by $^1$H-NMR still showed compound A to be present, thus, more cyclohexadiene and Pd black were added and the mixture was allowed to stir for 16 hours at 50° C. The catalyst was removed by filtration through celite, and the solvent was evaporated under reduced pressure. The crude material was chromatographed on silica gel (2% MeOH—$CH_2Cl_2$) which gave 3.2 g (75%) of the $C_4$-hydro product, compound CC.

What is claimed is:

1. A compound of the formula:

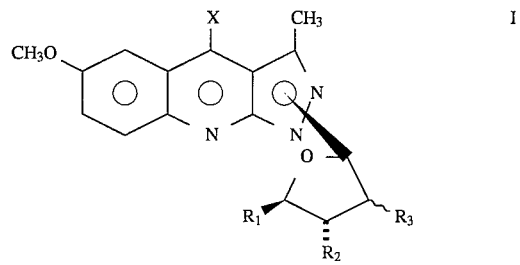

I wherein $R_1$ is HO—$CH_2$; ($C_1$-$C_6$)-alkyl-O—$CH_2$; $NH_2CH_2$; $PhCH_2COOCH_2$; $PhCH_2OCH_2$; $PhCOCH_2CH(OH)$; $PhCOCH_2CH_2$; $PhCONHCH_2$; ($C_1$-$C_6$)-alkyl—$COOCH_2$; PhCOCH=CH; $PhCOOCH_2$; or substituted-$PhCOOCH_2$, wherein the substituents are selected from the group consisting of ($C_1$-$C_6$) alkyl, ($C_1$-$C_6$) alkoxy, and nitro;

$R_2$ and $R_3$ are each independently HO; ($C_1$-$C_6$)-alkyl—COO; $PhCH_2COO$; $PhCH_2O$—; PhCOO—; substituted-PhCOO— wherein the substituents are selected from the group consisting of ($C_1$-$C_6$)alkyl, ($C_1$-$C_6$)alkoxy, and nitro; or $R_2$ and $R_3$ taken together can be a chemical bond;

and with the proviso that when the bond attached to the $R_2$ and the bond attached to the $R_3$ both extend below the plane of the page that $R_2$ and $R_3$ taken together can be

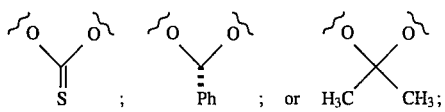

and

X is Cl or H;

or a stereoisomer thereof, or a pharmaceutically acceptable salt thereof.

2. A compound according to claim 1 of the formula

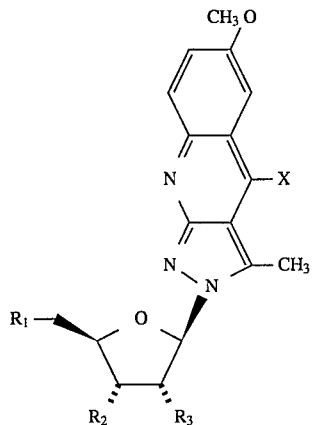

wherein $R_1$ is HO—$CH_2$; ($C_1$–$C_6$)-alkyl-O—$CH_2$; $NH_2CH_2$; $PhCH_2COOCH_2$; $PhCH_2OCH_2$; $PhCOCH_2C(OH,H)$; $PhCOCH_2CH_2$; $PhCONHCH_2$; ($C_1$–$C_6$)-alkyl-$COOCH_2$; PhCOCH=CH; $PhCOOCH_2$; or substituted-$PhCOOCH_2$, wherein the substituents are selected from the group consisting of ($C_1$–$C_6$)alkyl, ($C_1$–$C_6$)alkoxy, and nitro;

$R_2$ and $R_3$ are each independently HO; ($C_1$–$C_6$)-alkyl-COO; $PhCH_2COO$; $PhCH_2O$; PhCOO; substituted-Ph-COO wherein the substituents are selected from the group consisting of ($C_1$–$C_6$)alkyl, ($C_1$–$C_6$)alkoxy, and nitro; or $R_2$ and $R_3$ taken together can be a chemical bond;

and with the proviso that when the bond attached to the $R_2$ and the bond attached to the $R_3$ both extend below the plane of the page that $R_2$ and $R_3$ taken together can be

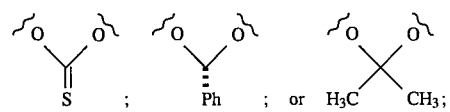

and

X is Cl or H;

or a stereoisomer thereof, or a pharmaceutically acceptable salt thereof.

3. A compound according to claim 1 selected from the group consisting of

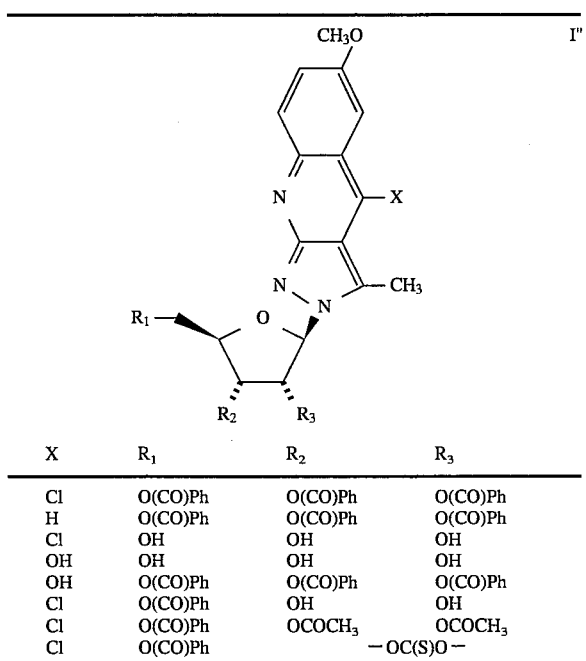

| X | $R_1$ | $R_2$ | $R_3$ |
|---|---|---|---|
| Cl | O(CO)Ph | O(CO)Ph | O(CO)Ph |
| H | O(CO)Ph | O(CO)Ph | O(CO)Ph |
| Cl | OH | OH | OH |
| OH | OH | OH | OH |
| OH | O(CO)Ph | O(CO)Ph | O(CO)Ph |
| Cl | O(CO)Ph | OH | OH |
| Cl | O(CO)Ph | $OCOCH_3$ | $OCOCH_3$ |
| Cl | O(CO)Ph | —OC(S)O— | | a pharmaceutically acceptable salt thereof.

4. The compound according to claim 1 of the formula

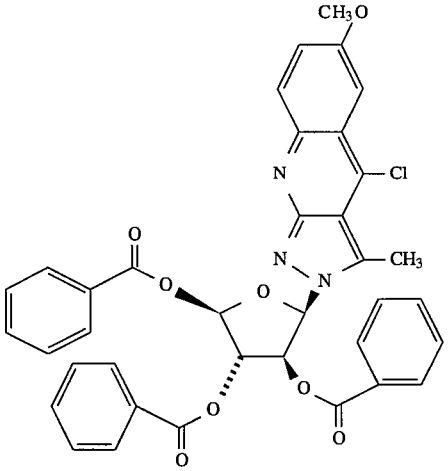

or a pharmaceutically acceptable salt thereof.

5. A compound according to claim 1 of the formula

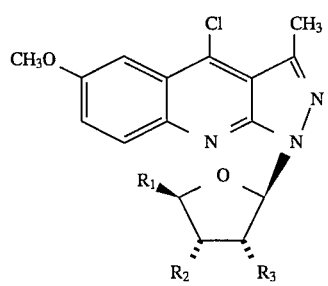

wherein $R_1$ is HO—$CH_2$; ($C_1$–$C_6$)-alkyl-O—$CH_2$; $NH_2CH_2$; $PhCH_2COOCH_2$; $PhCH_2OCH_2$; $PhCOCH_2C(OH,H)$; $PhCOCH_2CH_2$; $PhCONHCH_2$; ($C_1$–$C_6$)-alkyl-$COOCH_2$; PhCOCH=CH; $PhCOOCH_2$; or substituted-$PhCOOCH_2$, wherein the substituents are selected from the group consisting of ($C_1$–$C_6$)alkyl, ($C_1$–$C_6$)alkoxy, and nitro;

$R_2$ and $R_3$ are each independently HO; ($C_1$–$C_6$)-alkyl-COO; $PhCH_2COO$; $PhCH_2O$—; PhCOO—; substituted-PhCOO— wherein the substituents are selected from the group consisting of ($C_1$–$C_6$)alkyl, ($C_1$–$C_6$)alkoxy, and nitro; or $R_2$ and $R_3$ taken together can be a chemical bond;

and with the proviso that when the bond attached to the $R_2$ and the bond attached to the $R_3$ both extend below the plane of the page that $R_2$ and $R_3$ taken together can be

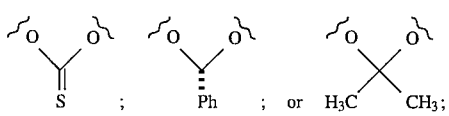

and

X is Cl or H;

or a stereoisomer thereof, or a pharmaceutically acceptable salt thereof.

6. A compound according to claim 4 wherein $R_1$ is $PhCOOCH_2$; or substituted-$PhCOOCH_2$, wherein the substituents are selected from the group consisting of ($C_1$–$C_6$)alkyl, ($C_1$–$C_6$)alkoxy, and nitro; or a pharmaceutically acceptable salt thereof.

7. A compound according to claim 5 wherein $R_1$ is $PhCOOCH_2$; or a pharmaceutically acceptable salt thereof.

8. A compound according to claim 5 wherein $R_2$ and $R_3$ are each independently $PhCOOCH_2$; or substituted-Ph-$COOCH_2$, wherein the substituents are selected from the group consisting of ($C_1$–$C_6$)alkyl, ($C_1$–$C_6$)alkoxy, and nitro; or a pharmaceutically acceptable salt thereof.

9. A compound according to claim 1 selected from the group consisting of

I'

| $R_1$ | $R_2$ | $R_3$ |
|---|---|---|
| O(CO)Ph | O(CO)Ph | O(CO)Ph |
| $OCOCH_3$ | $O(CO)CH_3$ | $O(CO)CH_3$ |
| $CH_2Ph$ | $CH_2Ph$ | $CH_2Ph$ |
| $O(CO)CH_2Ph$ | $(CO)CH_2Ph$ | $O(CO)CH_2Ph$ |
| O(CO)Ph-2,5-$(CH_3)_2$ | (CO)Ph-2,5-$(CH_3)_2$ | O(CO)Ph-2,5-$(CH_3)_2$ |
| O(CO)Ph-4-$CH_3O$ | (CO)Ph-4-$CH_3O$ | O(CO)Ph-4-$CH_3O$ |
| O(CO)Ph-4-$NO_2$ | (CO)Ph-4-$NO_2$ | O(CO)Ph-4-$NO_2$ |
| O(CO)Ph | OH | OH |
| OH | OH | OH |
| OH | | —OC$(CH_3)_2$—O— |
| O(CO)—$CH_2CH(CH_3)_2$ | O(CO)—$CH_2CH(CH_3)_2$ | O(CO)—$CH_2CH(CH_3)_2$ |
| C(H,OH)$CH_2$(CO)Ph | | —OC(S)O— |
| (CO)Ph | —OC(S)O— | |
| O(CO)Ph | —OC(Ph)O— | |
| O(CO)Ph | O(CO)—$CH_3$ | O(CO)—$CH_3$ |
| O(CO)Ph | —$CH_2Ph$ | —$CH_2Ph$ |
| O(CO)Ph | | — |
| NH2 | | —OC$(CH_3)_2$—O— |
| O(CO)PhNH | | —OC$(CH_3)_2$—O— |
| O(CO)PhNH | OH | OH | or a pharmaceutically acceptable salt thereof.

10. A compound according to claim 1 of the formula

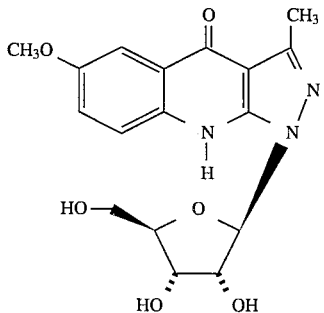

or a pharmaceutically acceptable salt thereof.

11. A compound according to claim 1 selected from the group consisting of

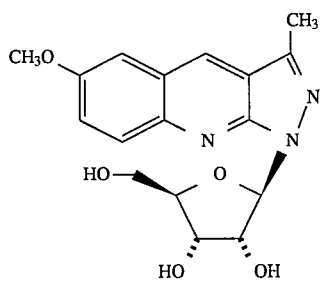

and

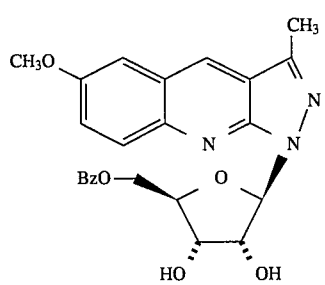

or a pharmaceutically acceptable salt thereof.

12. A compound according to claim 1 of the formula

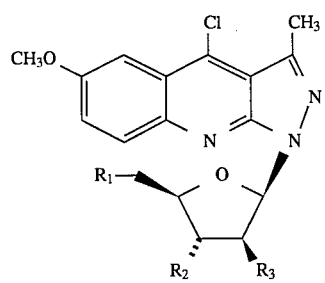

wherein $R_1$ is HO—$CH_2$; ($C_1$-$C_6$)-alkyl-O—$CH_2$; $NH_2CH_2$; $PhCH_2COOCH_2$; $PhCH_2OCH_2$; $PhCOCH_2CH(OH)$—; $PhCOCH_2CH_2$; $PhCONHCH_2$; PhCOCH=CH; $PhCOOCH_2$; or substituted-Ph-$COOCH_2$, wherein the substituents are selected from the group consisting of ($C_1$-$C_6$)alkyl, ($C_1C_6$)alkoxy, and nitro;

$R_2$ and $R_3$ are each independently HO; ($C_1$-$C_6$)-alkyl-COO; $PhCH_2COO$; $PhCH_2O$—; PhCOO—; substituted-PhCOO— wherein the substituents are selected from the group consisting of ($C_1$-$C_6$)alkyl, ($C_1$-$C_6$)alkoxy, and nitro; or $R_2$ and $R_3$ taken together can be a chemical bond;

or a stereoisomer thereof, or a pharmaceutically acceptable salt thereof.

13. The compound according to claim 1 of the formula

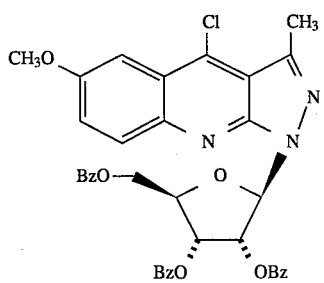

or a pharmaceutically acceptable salt thereof.

14. The compound of the formula

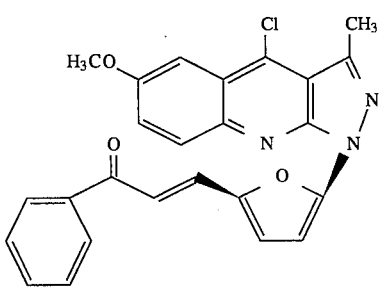

or a pharmaceutically acceptable salt thereof.

15. The compound of the formula

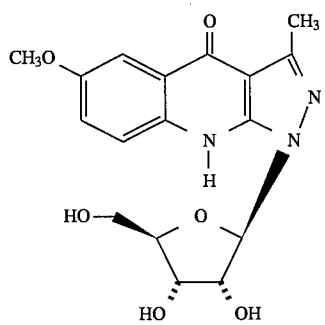

or a pharmaceutically acceptable salt thereof.

16. A composition comprising an antitumor effective amount of a compound according to claim 1 and a pharmaceutically acceptable carrier material.

17. A method for treating a tumor, wherein said tumor is treatable by a compound according to claim 1 which inhibits the binding of $^3$H-GDP to the ras p21 protein, which comprises administering an antitumor effective amount of said compound to a mammal in need thereof.

* * * * *